US006509163B1

(12) United States Patent
Buell et al.

(10) Patent No.: US 6,509,163 B1
(45) Date of Patent: Jan. 21, 2003

(54) METHODS OF SCREENING MODULATORS OF MAMMALIAN P2X₇ PURINERGIC RECEPTORS

(75) Inventors: Gary Nutter Buell, Geneva (CH); Annmarie Surprenant, Geneva (CH); Eric Kawashima, Geneva (CH)

(73) Assignee: Glaxo Group Limited, Middlesex (GB)

( * ) Notice: Subject to any disclaimer, the term of this patent is extended or adjusted under 35 U.S.C. 154(b) by 1 day.

(21) Appl. No.: 09/638,857

(22) Filed: Aug. 15, 2000

Related U.S. Application Data

(63) Continuation of application No. 08/842,079, filed on Apr. 28, 1997, now Pat. No. 6,133,434.

(51) Int. Cl.⁷ ..................... G01N 33/53; G01N 33/567; C12P 21/06; C12P 21/04; C12N 15/74
(52) U.S. Cl. ..................... 435/7.2; 435/69.1; 435/70.1; 435/471
(58) Field of Search .............................. 435/69.1, 70.1, 435/71.1, 71.2, 252.3, 320.1, 325, 471, 7.2

(56) References Cited

U.S. PATENT DOCUMENTS 5,360,893 A  11/1994  Owens et al.

FOREIGN PATENT DOCUMENTS

WO  WO 95/33048  12/1995

OTHER PUBLICATIONS

Coutinho–Silva et al. , Characterization of p2z purinergic receptors on phagocytic cells of the thymic reticulum in culture (Apr. 26, 1996), Biochem. et Biophys. Acta, 1280: 217–218.*
Wiley JS et al. , The P2z–purinoceptor of human lymphocytes: actions of nucleotide agonists and irreversible inhibition by oxidized ATP (1994) Br. J. Pharmacol. 112: 947–950.*
Suprenant A, The cytosolic P2z receptor for endogenous ATP identified as a P2X receptor (P2X7). (May 3, 1996), Science 272: 735–737.*
Rassendren F, The permeabilizing ATP receptor, P2X7 ( Feb. 28, 1997) J of Biol. Chem. 28: 5482–86.*
Molecular Probes Catalogue Supl. Cell Biology and Imaging. p5. Molecular Probes, Inc. Eugene, OR. 2001.*
Bo et al., "Solubilization and Molecular Size Determination of the $P_{2x}$ Purinoceptor from Rat Vas Deferens*", The Journal of Biological Chemistry, vol. 267, No. 25, Sep. 5, 1992, pp. 17581–17587.
Buell et al., "Mini–Review P2X Receptors: An Emerging Channel Family", European Journal of Neuroscience, vol. 8, 1996, pp. 2221–2228.

Owens et al., "Identification of mRNAs Associated with Programmed Cell Death in Immature Thymocytes", Molecular and Cellular Biology, vol. 11, No. 8, Aug. 1991, pp. 4177–4188.
Simon et al., "Solubilisation and Molecular Characterisation of the $P_{2x}$ Purinoceptor", Biochemical Society Transactions, vol. 21, No. 2, May 1993, p. 200S.
Surprenant et al., "The Cytolytic $P_{2Z}$ Receptor for Extracellular ATP Identified as a $P_{2x}$ Receptor (P2X₇)", Science, vol. 272, May 3, 1996, pp. 735–738.
Valera et al., "A New Class of Ligand–Gated Ion Channel Defined by $P_{2x}$ Receptor for Extracellular ATP", Nature, vol. 371, Oct. 6, 1994, pp. 516–519.
GenBank Accession No. Y09561, H. sapiens mRNA for P2X7 receptor, accessed Dec. 20, 1998.
Valera et al., "Characterization and chromosomal localization of a human P2X receptor from urinary bladder", Receptors and Channels 3(4):283–289 (1995).
An ATP–gated cation channel with some P2Z–like characteristics in gastric smooth muscle cells of toad, J. Physiol. 498(Pt. 2):427–442 (1997).
Rassendren et al, "The premeabilizing ATP receptor, P2X7", J. Biol. Chem. 272(9):5482–5486 (1997).
Murgia et al, "Oxized ATP", J. Biol. Chem. 268(11):8199–8293 (1997).
Buell et al, "P2X receotprs: an emerging channel family", Eur. J. Neurosci. 8(10):2221–2228 (1996).
GenBank Accession No. X95882, R. novegicus mRNA for ATP ligand gate ion channel, accessed Dec. 20, 1998.
Humphreys et al, Induction of the P2Z/P2X7 nucleotide receptor and associated phospholopase D activity by lipopolysaccharide adn INF–gamma in the human THP–1 monocytic cell line, J. Immunol. 157(12):5627–5637 (1996).
Di Virgilio et al, "A purinergic hypothesis for immunomoldulation", Ital. J. Biochem. 45(4):195–203 (1996).
Dubyak et al, "Expression of multiple ATP receptor subtypes during the differentiation and inflammatory activation of myeloid leukocytes", Drug Dev. Res. 39:269–278 (1996).
Wiley et al, "P22z–purinoceptor of human lymphocytes: actions of nucleotide agonists and irreversible inhibition by oxidized ATP", Br. J. Pharmacol. 112:946–950 (1994).

* cited by examiner

Primary Examiner—Gary L. Kunz
Assistant Examiner—Robert S. Landsman
(74) Attorney, Agent, or Firm—Nixon & Vanderhye P.C.

(57) ABSTRACT

The present invention relates, in general, to a purinergic receptor and, particular, to a P2X₇ (also designated P2Z) receptor. The invention further relates to a nucleic acid encoding the P2X₇ receptor and to a method of producing P2X₇ combinantly using same. The invention also relates to a method of screening compounds for their ability to inhibit P2X₇ activity and thereby for their usefulness in treating a variety of diseases/disorders, including arthritic and respiratory disorders and neurodegenerative diseases.

13 Claims, 21 Drawing Sheets

```
P2X7  M------PACCSWNDVFQYETNKVTRIQSVNYGTIKWILHMTVFSY-VSFALMSDKLYQRKEP-LISSVHTKVKGVAEVTENVTEG    78
      M       C  W    YET KV   G           Y V       KYQ E   SS   TKVKG    V
P2X2  MVRRLARGC--WSAFWDYETPKVIVVRNRRLGFVHRMVQLLILLYFV-WYVFIVQKSYQDSETGPESSIITKVKGITMSEDKV--      80

P2X7  GVTKLVHGIFDTADYTLPLQGNSFF-VMTNYLKSEGQEQKLCPE-YPSRGKQCHSDQGCIKGWMDPQSKGIQTGRCIPY-DQKRK    160
              D   YPGS  T        Q    CPE          CHSD  CI G D Q GI TG C PY     K
P2X2  ------WDVEEYVKPPEGGSVVSIITRIEVTPSQTLGTCPESMRVHSSTCHSDDDCIAGQLDMQGNGIRTGHCVPYYHGDSK       156

P2X7  TCEIFAWCPAEEGKEAPRPALLRSAENFTVLIKNNIDFPGHNYTTRNILPGMNI---SCTFHKTWNPOCPIFRLGDIFQEIGENF    242
      TCE  AWCPEG        L    A NFT LIKN I  P        NI       CTF    P CPIFRLG I      GENF
P2X2  TCEVSAWCPVEDG-TSDNHFLGKMAPNFTILIKNSIHYPKFKFSKGNIASQKSDYLKHCTFDQDSDPYCPIFRLGFIVEKAGENF    240

P2X7  TEVAVQGGIMGIEIYWDCNLDSWSHRCQPKYSFRRLDDKYTNESLFPGYNFRYAKYYKENGMEK-RTLIKAFGVRFDILVFGTGG    326
      TE A   GG I G I W C  LD        C PKYS RRLD KY   S        A YYK NG   RTLIKA G R D VG G
P2X2  TELAHKGGVIGVIINWNCDLDLSESECNPKYSFRRLDPKYDPAS--SGYNFRFAKYYKINGTTTRTLIKAYGIRIDVIVHGQAG    323

P2X7  KFDIIQLVVYIGSTLSYFGLATVCIDLIINTYASTCCRSRVYPSCKCCEPIVEPKPTLKYVSFVDEPHIWM                   411
      KF I       L  G      DI  T                K
P2X2  KFSLIPTIINLATALTSIGVGSFLCDWILLTFMNKNKLYSHKKFDKVRTPKHPSSRWPVTLALVLGQIPPPSHYSQDQPPSPPS    408

P2X7  VDQQLLGKSLQDVKGQEVPRPQTDFLELSRLSLSLHHSPPIPGQPEEMQLLQIEAVPRSRDSPDWCQCGNCLPSQLPENRRALEE    496
             L                                           E
P2X2  GEGPTLGEGAELPLAVQSPRPCSISALTEQVVDTLGQHMGQRPPVPEPSQQDSTSTDPKGLAQL                         492

P2X7  LCCRRKPGQCITTSELFSKIVLSREALQLLLLYQEPLLALEGEAINSKLRHCAYRSYATWRFVSQDMADFAILPSCCRWKIRKEF    581

P2X7  PKTQGQYSGFKYPY                                                                           595
```

```
rP2X7 X95882 -> Genes
DNA  sequence    3540 b.p.    ttaaacgttcct ... cacactcacaca    linear 1 ttaaacgttcctgctaagtaatcgtgtgcttcttcctcggtgtgcctactcctcgtgtggggcttgctgtggtctagcctgggaag  80
  81 gtctagcccagtccccgcgaaacagagtgagcctgtcgcc ATG CCG GCT TGC TGC AGC TGC AGC TGG AAC GAT   148
                                              M   P   A   C   C   S   C   S   W   N   D     9
 149 GTC TTT CAG TAT GAG ACA AAC AAA GTC ACC CGG ATC CAG AGC GTG AAT TAC GGC ACC ATC        208
  10  V   F   Q   Y   E   T   N   K   V   T   R   I   Q   S   V   N   Y   G   T   I        29
 209 AAG TGG ATC TTG CAC ATG ACC ATG TTC TCC TAC GTT GTT TTT GCT TTG ATG AGC GAC AAG        268
  30  K   W   I   L   H   M   T   M   F   S   Y   V   V   F   A   L   M   S   D   K        49
 269 CTA TAT CAG CGG AAG GAG CCC CTT ATC AGC TCT GTG CAC ACC AAG GTC AAA GGC GTT GCA        328
  50  L   Y   Q   R   K   E   P   L   I   S   S   V   H   T   K   V   K   G   V   A        69
 329 GAG GTG ACA GAG AAT GTC ACG GAG GGC GTG AAG TTA GTA CAC GGC ATC TTC GAC                388
  70  E   V   T   E   N   V   T   E   G   V   K   L   V   H   G   I   F   D                89
 389 ACG GCC GAC TAC ACC CTC CCT TTG CAG GGG AAC TCG TTC TTT GTA ATG ACA AAT TAT CTC        448
  90  T   A   D   Y   T   L   P   L   Q   G   N   S   F   F   V   M   T   N   Y   L        109
 449 AAG TCA GAA GGC CAA GAA CTG TGT CCT GAG TAT CCC AGC CGG GGT AAA CAG ATC CAG TGC        508
 110  K   S   E   G   Q   E   L   C   P   E   Y   P   S   R   G   K   Q   I   Q   C        129
 509 CAT TCT GAC CAG GGT TGT ATA AAA GGA TGG ATG GAC CCA CAA AGT AAG GGA ATC CAG ACC        568
 130  H   S   D   Q   G   C   I   K   G   W   M   D   P   Q   S   K   G   I   Q   T        149
 569 GGC AGG TGT ATA CCT TAC GAC CAG AAG AGG AAG ACC TGT GAA ATC TTT GCC TGG TGT CCT        628
 150  G   R   C   I   P   Y   D   Q   K   R   K   T   C   E   I   F   A   W   C   P        169
 629 GCT GAG GGG AAA GAA GCC CCA CGG CCT GCA CTC TTG AGG AGC GCC GAA AAC TTC ACC            688
 170  A   E   G   K   E   A   P   R   P   A   L   L   R   S   A   E   N   F   T            189
 689 GTA CTC ATC AAG AAC AAT ATC GAC TTC CCG GGC CAC AAC TAT ACT ACG AGG AAC ATA TTA        748
 190  V   L   I   K   N   N   I   D   F   P   G   H   N   Y   T   T   R   N   I   L        209
```

Figure 1B-2 rP2X7 X95882 -> Genes

```
 749 CCA GGT ATG AAC ATC TGT TGT ACC TTT CAC AAG ACT TGG AAC CCT CAG TGT CCC ATC TTC  808
 210  P   G   M   N   I   C   C   T   F   H   K   T   W   N   P   Q   C   P   I   F  229

809 CGG CTA GGG GAC ATC CAG TTC TTC GGC TAC GAG AAC TTT ACA GAG GTG GCA GTT CAG GGA  868
 230  R   L   G   D   I   Q   F   F   G   Y   E   N   F   T   E   V   A   V   Q   G  249

869 GGA ATC ATG GGC ATT GAG ATC TAC TGG GAC TGC AAC CTG GAC AGC TGG TCC CAT CGC TGT  928
 250  G   I   M   G   I   E   I   Y   W   D   C   N   L   D   S   W   S   H   R   C  269

929 CAA CCC AAA TAC AGC TTC AGA CGG CTG GAC GAC AAG TAC ACC AAT GAG TCC CTG TTC CCT  988
 270  Q   P   K   Y   S   F   R   R   L   D   D   K   Y   T   N   E   S   L   F   P  289

989 GGC TAC AAC TTC AGA TAC GCC AAG TAC TAT AAG GAA AAT GGC ATG GAA AAG CGG ACA TTG  1048
 290  G   Y   N   F   R   Y   A   K   Y   Y   K   E   N   G   M   E   K   R   T   L  309

1049 ATC AAA GCC TTC GGC GTG CGT TTT GAC ATC CTG GTT TTT GGC ACT GGA GGA AAG TTT GAC  1108
 310  I   K   A   F   G   V   R   F   D   I   L   V   F   G   T   G   G   K   F   D  329

1109 ATC ATC CAG TTG GTT GTG TAC ATT GGA TCC ACC CTG TCC TAT TTC GGT TTG GCC ACC GTG  1168
 330  I   I   Q   L   V   V   Y   I   G   S   T   L   S   Y   F   G   L   A   T   V  349

1169 TGT ATT GAC TTG ATC ATC AAC ACG TAT GCC AGT ACC TGC TGC AGG TCA CGT GTT TAC CCC  1228
 350  C   I   D   L   I   I   N   T   Y   A   S   T   C   C   R   S   R   V   Y   P  369

1229 TCC TGT AAG TGC TGC GAG CCC TGT GCA GTG AAT GAG TAC TAC TAC AGA AAG AAG TGT GAG  1288
 370  S   C   K   C   C   E   P   C   A   V   N   E   Y   Y   Y   R   K   K   C   E  389

1289 CCC ATC GTG GAG CCC AAG CCG ACG TTA AAG TAT GTG TCC TTT GTG GAT GAG CCC CAC ATT  1348
 390  P   I   V   E   P   K   P   T   L   K   Y   V   S   F   V   D   E   P   H   I  409

1349 TGG ATG GTG GAC CAG CAG CTG CTT GGG AAA AGT CTG CAA GAT GTC AAA GGT CAA GAG GTC  1408
 410  W   M   V   D   Q   Q   L   L   G   K   S   L   Q   D   V   K   G   Q   E   V  429

1409 CCG AGA CCC CAG ACG GAC TTC TTG GAA CTG TCT AGG CTC TCC CTC CAC CAC TCA  1468
 430  P   R   P   Q   T   D   F   L   E   L   S   R   L   S   L   H   H   S  449
```

*Figure 1B-3*

```
rP2X7 X95882 -> Genes

1469 CCC CCA ATT CCT GGA CAA CCT GAG GAA ATG CAG GAA CTG CTC CAG ATA GAA GCG GTT CCT AGG  1528
 450  P   P   I   P   G   Q   P   E   E   M   Q   E   L   L   Q   I   E   A   V   P   R   469

1529 TCC AGG GAC AGC CCA GAT TGG TGC CAG TGT GGA AAC TGC CTC CCG TCT CAA CTA CCA GAG  1588
 470  S   R   D   S   P   D   W   C   Q   C   G   N   C   L   P   S   Q   L   P   E   489

1589 AAC CGC AGG GCC CTG GAG GAG CTG TGC TGC CGG AAG AAG CCA GGA GCC TGC ATC ACT ACC  1648
 490  N   R   R   A   L   E   E   L   C   C   R   K   K   P   G   A   C   I   T   T   509

1649 TCT GAG CTC TTC AGT AAG ATC GTG CTA TCC AGA GAG GCC CTG CAG CTC CTG CTC TAC  1708
 510  S   E   L   F   S   K   I   V   L   S   R   E   A   L   Q   L   L   L   Y   529

1709 CAG GAG GAG CCC TTG GCG CTG GAG GGA CTG GCC ATC AAC AGC AAG CTG CGA CAC CAC GCG  1768
 530  Q   E   E   P   L   A   L   E   G   L   A   I   N   S   K   L   R   H   C   A   549

1769 TAC AGG AGC TAT GCC ACC TGG CGC TTT GTC TCC CAA GAC ATG GCC GAC TTT GCC ATT CTG  1828
 550  Y   R   S   Y   A   T   W   R   F   V   S   Q   D   M   A   D   F   A   I   L   569

1829 CCC AGC TGC TGC CGC TGG AAG ATC CGG AAG GAG TTC CCC AAG ACC CAG GGG CAG TAC AGT  1888
 570  P   S   C   C   R   W   K   I   R   K   E   F   P   K   T   Q   G   Q   Y   S   589

1889 GGC TTC AAG TAT CCC TAC TGA cagtatggctgccacattatggtgactcatatagcattctcttggaaag   1961
 590  G   F   K   Y   P   Y   *                                                        596

1962 acttagagacacacttcagcaaagggaacttaagtcttcctccctcgtaagcgtgttgaaggattgttaggccaa       2041

2042 tggcaagcacatgaaccctccacgtggatgagaaacagatgcagatctgagcctgagcttgacctgacctgcgtg       2121

2122 ccaccacacagcctataacgtatacacaggctcctgatcccgatctcccaactcactcctctgaactagcattgtg       2201

2202 gagacggtgaaggtgttttctctccgtccatgtccttcctgatacagaggccattcctgaaaaccaaacc          2281

2282 tttgagattcgagagtactctgagaaatgaaatatggccacaaattcttttgacgtcctccaccccaaccccctca    2361
```

*Figure 1B-4* rP2X7 X95882 -> Genes

```
2362  agacccaaaggtgtcgttccccctcccattacgggcaactctggcggcttcatccagtagcggatgtgacgtcacatgt  2441
2442  attgttcaggcccctagtttaagaggctaacacttccaattcctgtgaacgcttgctgagaggaagccaggcaagtt  2521
2522  aagagcacaactataggggcttctcggctgtgaggaagcccgagaagcccaggggaagtaatcaacctgagccagctc  2601
2602  atcaccagaagctgccacggcaggtgattccagacacgtgactgaaactgcaggagacgaactgcgcatgtcaa    2681
2682  cccagaggaccactctgctgccttgtcgttacatgtggggagtgcggtccacacacagcaacaggcaaccggagcaaggg  2761
2762  atgctaaccgaggcccgagtcactgcaaagctagagactccttatatcggcaactttaagaggtcacattaaccagac  2841
2842  tagaagccatcgcatctaaccgatctgtgcctttaacgtcctgactgaacagtgagtccgaggcaatctaatgcc   2921
2922  ggcagaaaccactaaagcgcctctgtgcctctgcctttaacgtcctgactgaacagtgagtccgaggcaatctaatgcc  3001
3002  tcagcctagtgcctttggggggcggggggtcagagagaggggtgtctcctggaactggaattgcagtggatatgagtacc  3081
3082  gtgtggtcctgggaagtgaacttgagcctctgagcgtgctgtgcctcttaaccactgagcgtcctacacccttc   3161
3162  acaaccacacatcttaaaaatcataatcataatagagaaaagagagggaagagcgcctggggaggtggttcagtgggtaa  3241
3242  gagcacaagcatgagaccctttgttggatcacagcatccacctaaagtttgatgtggcttggtagagacaggaggggtg  3321
3322  ggggtgggggtgagcttgccatgtaatctgatgacctttgaaccccatggtgaatgtggagaatcacgttcctgact  3401
3402  tccacatgacctcacacacacacacacacacactacccacacagacacacaccaacacacaagcacacacatacaca  3481
3482  tgaagacacagagacatatacacactaccaccacaaccactaccacacactcacaca  3540
```

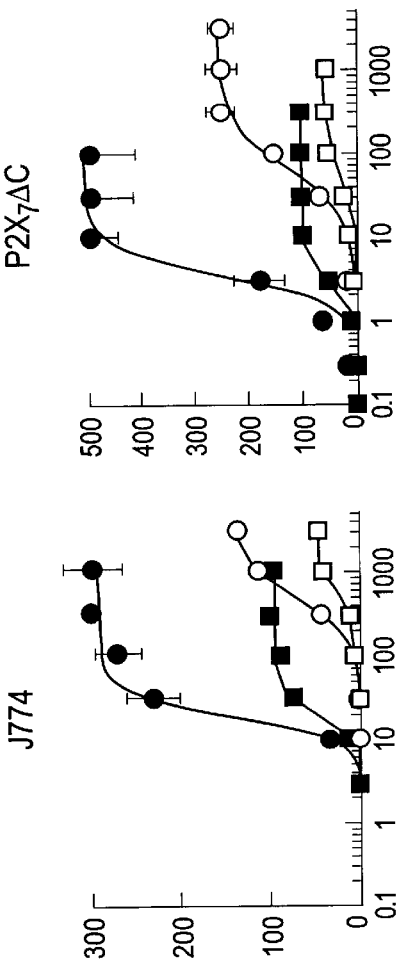
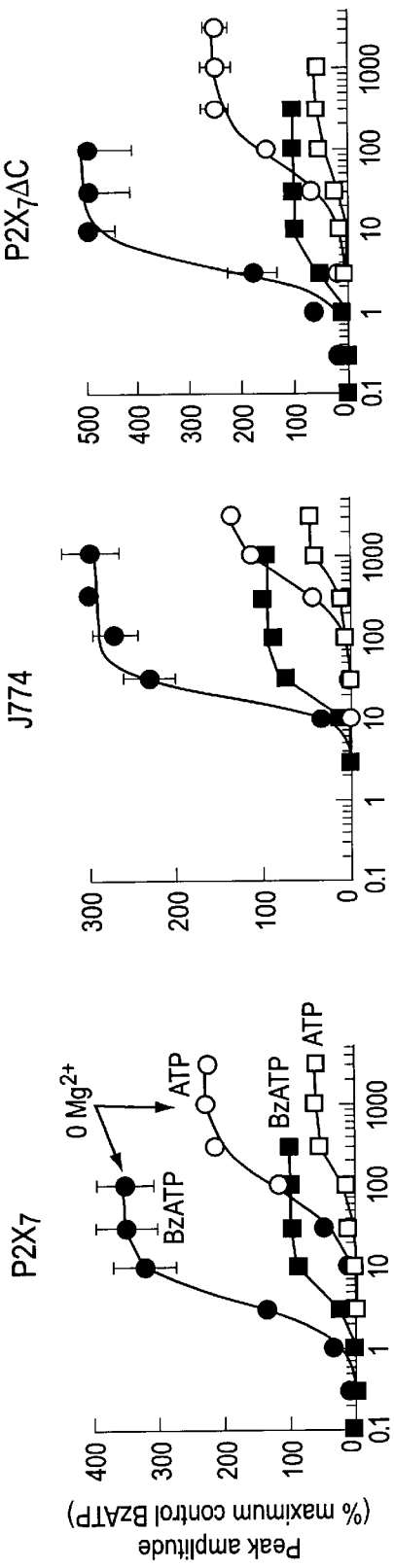
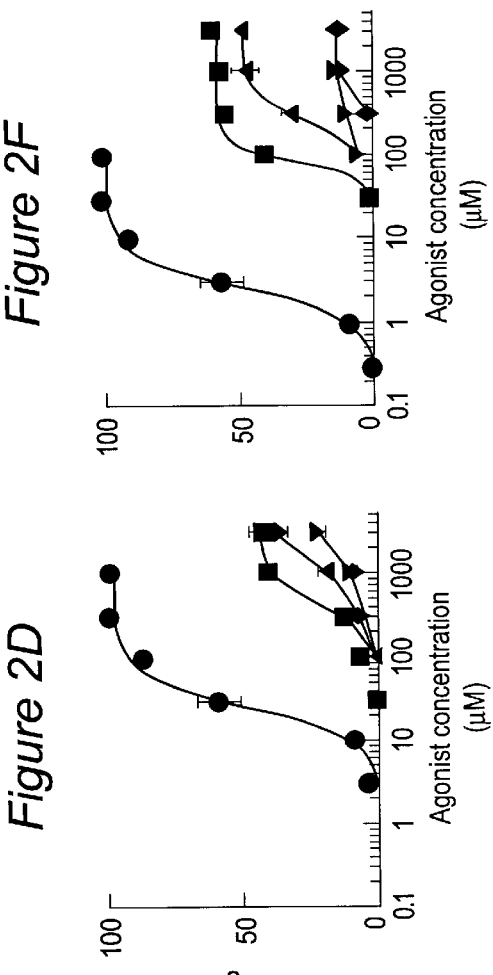
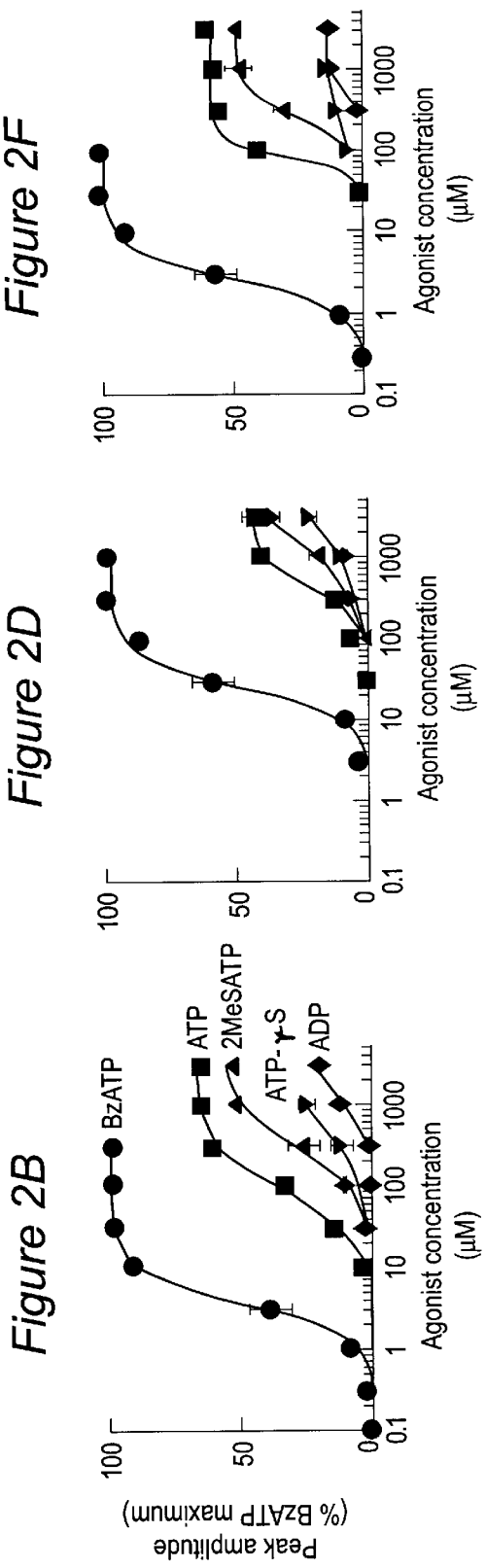
Figure 2A  Figure 2C  Figure 2E
Figure 2B  Figure 2D  Figure 2F

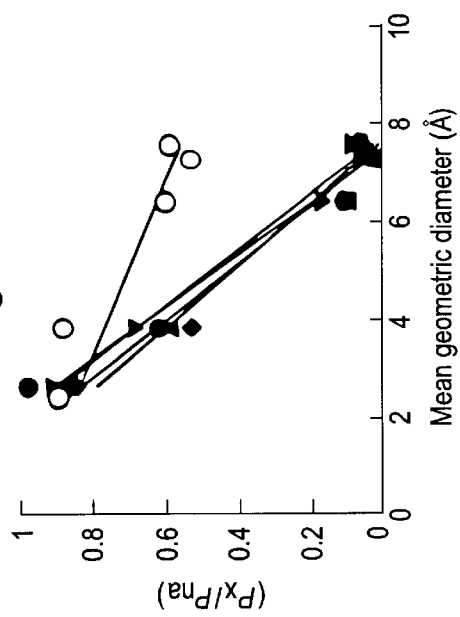
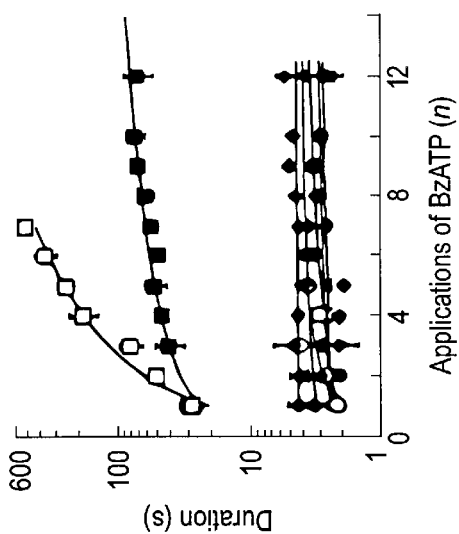
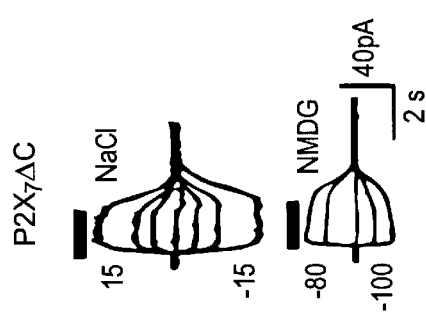
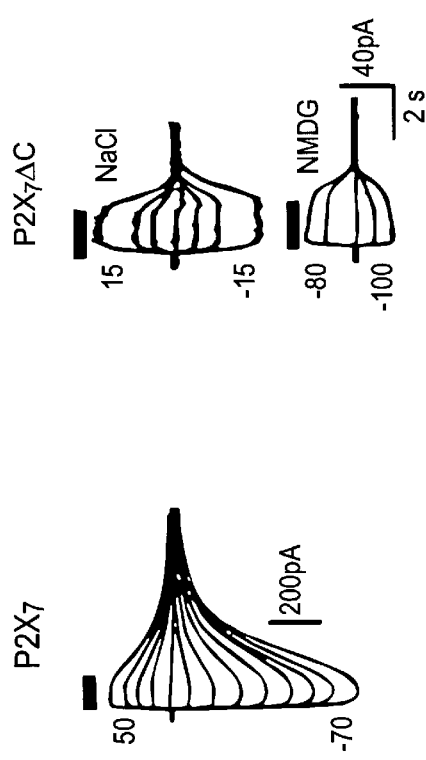
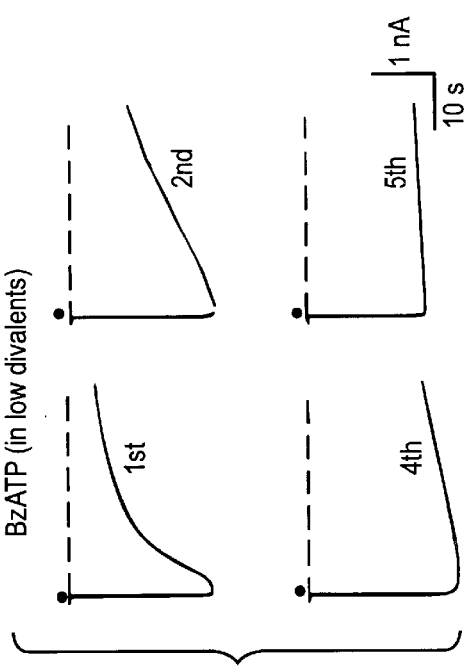

Figure 5A

```
rP2X7    1   MPACCSWNDVFQYETNKVTRIQSVNYGTIKWILHMTVFSYVSFALMSDKLYQRKEPLISS
hP2X7    1   MPACCSCSDVFQYETNKVTRIQSMNYGTIKWFFHVIIFSYVCFALVSDKLYQRKEPVISS
                 **   ******* **************  **  ****  **  ***********  **
                                                                         * rP2X7    61  VHTKVKGVAEVTENVTEGGVTKLVHGIFDTADYTLPLQGNSFFVMTNYLKSEGQEQKLCP
hP2X7    61  VHTKVKGIAEVKEEIVENGVKKLVHSVFDTADYTFPLQGNSFFVMTNFLKTEGQEQRLCP
                 ******  *** * *** ******  ******* ***********  ** ***** ***
                                                                         * rP2X7    121 EYPSRGKQCHSDQGCIKGWMDPQSKGIQTGRCIPYDQKRKTCEIFAWCPAEEGKEAPRPA
hP2X7    121 EYPTRRTLCSSDRGCKKGWMDPQSKGIQTGRCVVHEGNQKTCEVSAWCPIEAVEEAPRPA
                 ***    * ** ** ****************  *   *** **  **** *   *****
                                                                         *** rP2X7    181 LLRSAENFTVLIKNNIDFPGHNYTTRNILPGMNISCTFHKTWNPQCPIFRLGDIFQEIGE
hP2X7    181 LLNSAENFTVLIKNNIDFPGHNYTTRNILPGLNITCTFHKTQNPQCPIFRLGDIFRETGD
                  ***********************   **** **********   * * rP2X7    241 NFTEVAVQGGIMGIEIYWDCNLDSWSHRCQPKYSFRRLDDKYTNESLFPGYNFRYAKYYK
hP2X7    241 NFSDVAIQGGIMGIEIYWDCNLDRWFHHCHPKYSFRRLDDKTTNVSLYPGYNFRYAKYYK
                 ** ** ****************  *  * ***********  *  * ***********
                                                                         * rP2X7    301 ENGMEKRTLIKAFGVRFDILVFGTGGKFDIIQLVVYIGSTLSYFGL ATVCIDLIINTYAS
hP2X7    301 ENNVEKRTLIKVFGIRFDILVFGTGGKFDIIQLVVYIGSTLSYFGL AAVFIDFLIDTYSS
                 ** ******** ** ******************************   * ** * ** *
                                                                         * rP2X7    361 TCCRSRVYPSCKCCEPCAVNEYYYRKKCEPIVEPKPTLKYVSFVDEPHIWMVDQQLLGKS
hP2X7    361 NCCRSHIYPWCKCCQPCVVNEYYYRKKCESIVEPKPTLKYVSFVDESHIRMVNQQLLGRS
                 ****  *** ****  ** ********* **************** ** ** *****
                                                                         * rP2X7    421 LQDVKGQEVPRPQTDFLELSRLSLSLHHSPPIPGQPEEMQLLQIEAVPRSRDSPDWCQCG
hP2X7    421 LQDVKGQEVPRLAMDFTDLSRLPLALHDTPPIPGQPEEIQLLRKEATPRSRDSPVWCQCG
                 ***********   **  ****  *  *  ******** *** ** ******* ****
                                                                         * rP2X7    481 NCLPSQLPENRRALEELCCRRKPGQCITTSELFSKIVLSREALQLLLYQEPLLALEGEA
hP2X7    481 SCLPSQLPESHRCLEELCCRKKPGACITTSELFRKLVLSRHVLQFLLLYQEPLLALDVDS
                 *********    ***** **** ******** * ****  ** *********    *
                                                                         * rP2X7    541 INSKLRHCAYRSYATWRFVSQDMADFAILPSCCRWKIRKEFPKTGQYSGFKYPY
hP2X7    541 TNSRLRHCAYRCYATWRFGSQDMADFAILPSCCRWRIRKEFPKSEGQYSGFKSPY
                 *** ****** ****** ****************  ******  ******  *
                                                                         *
```

Figure 5B-1

```
hP2X7 seq submission 11/96  -> Genes
DNA    sequence     1853 b.p.      AAAACGGAGGA ... ATCCCACTTTT   linear 1 AAAACGGAGGAGGGGCTGTCACC ATG CCG GCC TGC TGC AGC TGC AGT GAT GTT TTC CAG TAT    65
  1                          M   P   A   C   C   S   C   S   D   V   F   Q   Y    13

66 GAG ACG AAC AAA GTC ACT CGG ATC CAG AGC ATG AAT TAT GGC ACC ATT AAG TGG TTC TTC  125
 14  E   T   N   K   V   T   R   I   Q   S   M   N   Y   G   T   I   K   W   F   F   33

126 CAC GTG ATC ATC TTT TCC TAC GTT TGC TTT GCT CTG GTG AGT GAC AAG CTG TAC CAG CGG  185
 34  H   V   I   I   F   S   Y   V   C   F   A   L   V   S   D   K   L   Y   Q   R   53

186 AAA GAG CCT GTC ATC AGT TCT GTG CAC ACC AAG GTG AAG GGG ATA GCA GAG GTG AAA GAG  245
 54  K   E   P   V   I   S   S   V   H   T   K   V   K   G   I   A   E   V   K   E   73

246 GAG ATC GTG GAG AAT GGA GTG AAG AAG TTG GTG CAC AGT GTC TTT GAC ACC GCA GAC TAC  305
 74  E   I   V   E   N   G   V   K   K   L   V   H   S   V   F   D   T   A   D   Y   93

306 ACC TTC CCT TTG CAG GGG AAC TCT TTC TTC GTG ATG ACA AAC TTC CTC AAA ACA GAA GGC  365
 94  T   F   P   L   Q   G   N   S   F   F   V   M   T   N   F   L   K   T   E   G   113

366 CAA GAG CAG CGG CTT TGT CCC GAG TAT CCC ACC CGC AGG ACG CTC TGT TCC TCT GAC CGG  425
114  Q   E   Q   R   L   C   P   E   Y   P   T   R   R   T   L   C   S   S   D   R   133

426 GGT TGT AAA AAG GGA TGG ATG GAC CCA CAG AGC AAA GGA ATT CAG ACC GGA AGG TGT GTA  485
134  G   C   K   K   G   W   M   D   P   Q   S   K   G   I   Q   T   G   R   C   V   153

486 GTG CAT GAA GCT CCC CGG CCT CCT GCT CTC TTG AGG GTC TCT TCT GGA GCC ATC GAG GCA GTG  545
154  V   H   E   A   P   R   P   P   A   L   L   R   V   S   S   A   I   E   A   V   173

546 GAA GAG GCC GCC CCT GCT CTT CTT AAC AGT GCC GAA AAC TTC ACT GTG CTC ATC AAG  605
174  E   E   A   A   P   A   L   L   N   S   A   E   N   F   T   V   L   I   K   193

606 AAC AAT ATC GAC TTC CCC GGC CAC AAC TAC ACC ACG AGA AAC ATC CTG CCA GGT TTA AAC  665
194  N   N   I   D   F   P   G   H   N   Y   T   T   R   N   I   L   P   G   L   N   213
```

Figure 5B-2 hP2X7 seq submission 11/96 -> Genes

```
 666 ATC ACT TGT ACC TTC CAC AAG ACT CAG AAT CCA CAG TGT CCC ATT TTC CGA CTA GGA GAC  725
 214  I   T   C   T   F   H   K   T   Q   N   P   Q   C   P   I   F   R   L   G   D   233

726 ATC TTC CGA GAA ACA GGC GAT AAT TTT TCA GAT GTG GCA ATT CAG GGC GGA ATA ATG GGC  785
 234  I   F   R   E   T   G   D   N   F   S   D   V   A   I   Q   G   G   I   M   G   253

786 ATT GAG ATC TAC TGG GAC TGC AAC CTA GAC CGT TGG TTC CAT CAC TGC CAT CCC AAA TAC  845
 254  I   E   I   Y   W   D   C   N   L   D   R   W   F   H   H   C   H   P   K   Y   273

846 AGT TTC CGT CGC CTT GAC GAC AAG ACC ACC AAC GTG TCC TTG TAC CCT GGC TAC AAC TTC  905
 274  S   F   R   R   L   D   D   K   T   T   N   V   S   L   Y   P   G   Y   N   F   293

906 AGA TAC GCC AAG TAC TAC AAG GAA AAT AAT GTT GAG AAA CGG ACT CTG ATA AAA GTC TTC  965
 294  R   Y   A   K   Y   Y   K   E   N   N   V   E   K   R   T   L   I   K   V   F   313

966 GGG ATC CGT TTT GAC ATC CTG GTT TTT GGC ACC GGA GGA AAA TTT GAC ATT ATC CAG CTG 1025
 314  G   I   R   F   D   I   L   V   F   G   T   G   G   K   F   D   I   I   Q   L   333

1026 GTT GTG TAC ATC GGC TCA ACC CTC TCC TAC TTC GGT CTT GCC GCT GTT TTC ATC GAC TTC 1085
 334  V   V   Y   I   G   S   T   L   S   Y   F   G   L   A   A   V   F   I   D   F   353

1086 CTC ATC GAC ACT TAC TCC AGT AAC TGC TGC CGT TCG CAT ATT TAT CCC TGG TGC AAG TGC 1145
 354  L   I   D   T   Y   S   S   N   C   C   R   S   H   I   Y   P   W   C   K   C   373

1146 TGT CAG CCC TGT GTG GTC AAC GAA TAC TAC TAC AGG AAG AAG TGC GAG TCC ATT GTG GAG 1205
 374  C   Q   P   C   V   V   N   E   Y   Y   Y   R   K   K   C   E   S   I   V   E   393

1206 CCA AAG CCG ACA TTA AAG TAT GTG TCC TTT GTG GAT GAA AGC CAC ATT AGG ATG GTG AAC 1265
 394  P   K   P   T   L   K   Y   V   S   F   V   D   E   S   H   I   R   M   V   N   413

1266 CAG CAG CTA CTA GGG AGA AGT CTC CAA GAT GTC AAG GGC CAA GAA GTC CCA AGA CCT GCG 1325
 414  Q   Q   L   L   G   R   S   L   Q   D   V   K   G   Q   E   V   P   R   P   A   433

1326 ATG GAC TTC ACA GAT TTG TCC AGG CTC CCG CTG GCC CTC CAT GAC ACC CCG CCG ATT CCT 1385
 434  M   D   F   T   D   L   S   R   L   P   L   A   L   H   D   T   P   P   I   P   453
```

*Figure 5B-3* hP2X7 seq submission 11/96 -> Genes

```
1386 GGA CAA CCA GAG GAG ATA CAG CTG CTT AGA AAG GAG GCG ACT CCT AGA TCC AGG GGT AGC   1445
 454  G   Q   P   E   E   I   Q   L   L   R   K   E   A   T   P   R   S   R   D   S    473

1446 CCC GTC TGG TGC CAG TGT GGA AGC CTC CCA TCT CAA CTC CCT GAG CAC AGC TGC   1505
 474  P   V   W   C   Q   C   G   S   L   P   S   Q   L   P   E   H   R   C    493

1506 CTG GAG GAG CTG TGC TGC CGG AAA AAG CCG GGG GCC TGC ATC ACC ACC TCA GAG CTG TTC   1565
 494  L   E   E   L   C   C   R   K   K   P   G   A   C   I   T   T   S   E   L   F    513

1566 AGG AAG CTG GTC CTG TCC AGA CAC GTG CTG CAG TTC CTC CTC CTC TAC CAG GAG CCC TTG   1625
 514  R   K   L   V   L   S   R   H   V   L   Q   F   L   L   L   Y   Q   E   P   L    533

1626 CTG GCG CTG GAT GTG GAT TCC ACC AAC AGC CGG CTG CGG CAC TGT GCC TAC AGG TGC TAC   1685
 534  L   A   L   D   V   D   S   T   N   S   R   L   R   H   C   A   Y   R   C   Y    553

1686 GCC ACC TGG CGC TTC GGC TCC CAG GAC ATG GCT GAC TTT GCC ATC CTG CCC AGC TGC TGC   1745
 554  A   T   W   R   F   G   S   Q   D   M   A   D   F   A   I   L   P   S   C   C    573

1746 CGC TGG AGG ATC CGG AAA GAG TTT CCG AAG AGT GGC CAG TAC AGT GGG TTC AAG AGT   1805
 574  R   W   R   I   R   K   E   F   P   K   S   G   Q   Y   S   G   F   K   S    593

1806 CCT TAC TGA AGCCAGGCACCGTGGCTCAGTCTGTAATCCACTTTT   1853
 594  P   Y   *                                          596
```

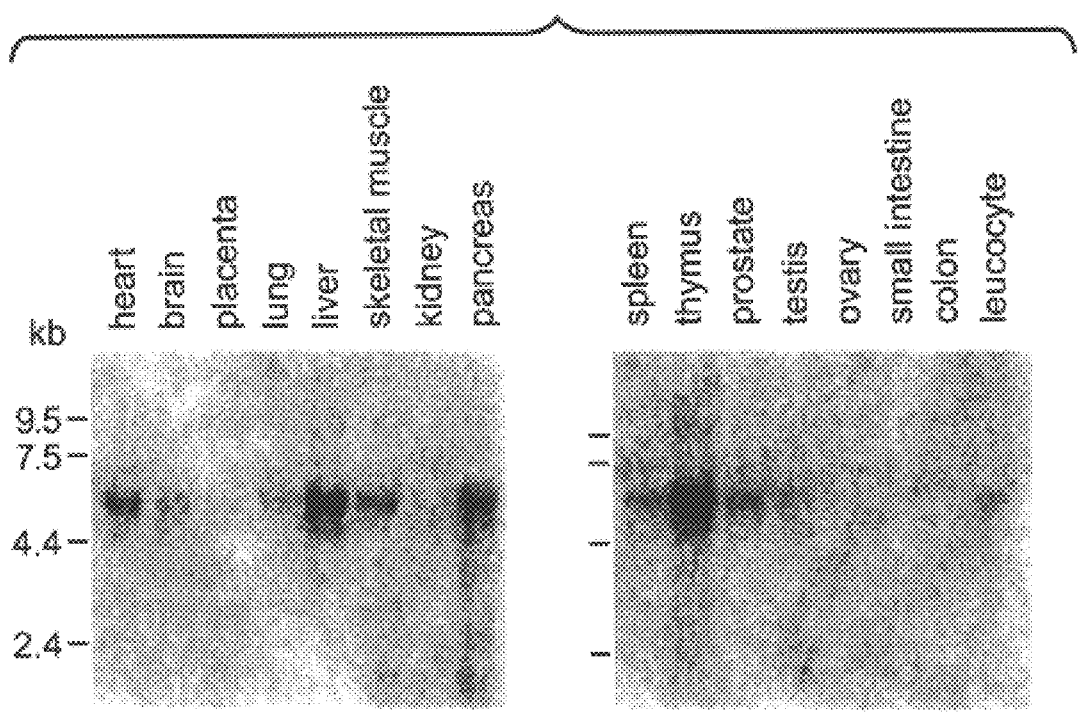

*human P2X$_7$ receptor expressed in HEK293 cells*

*human macrophage*

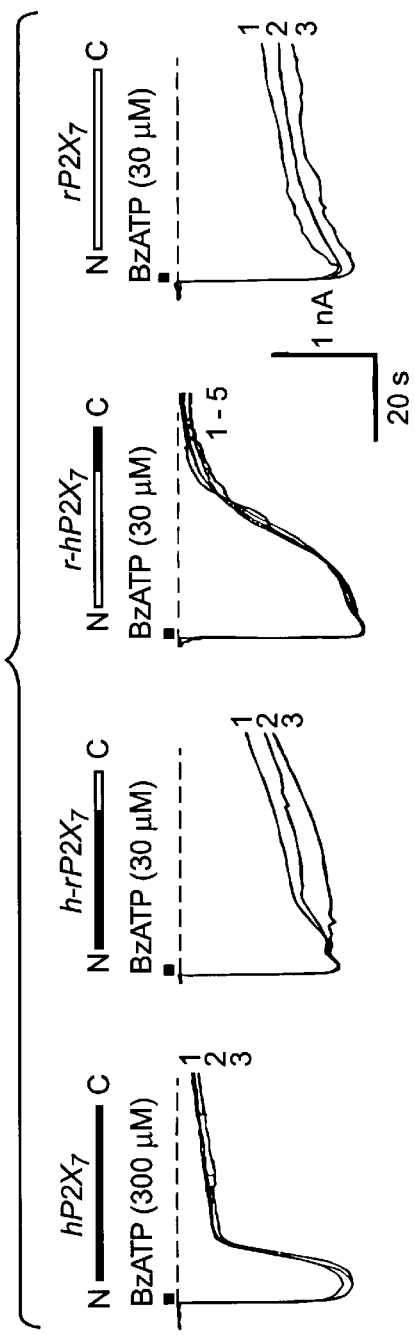
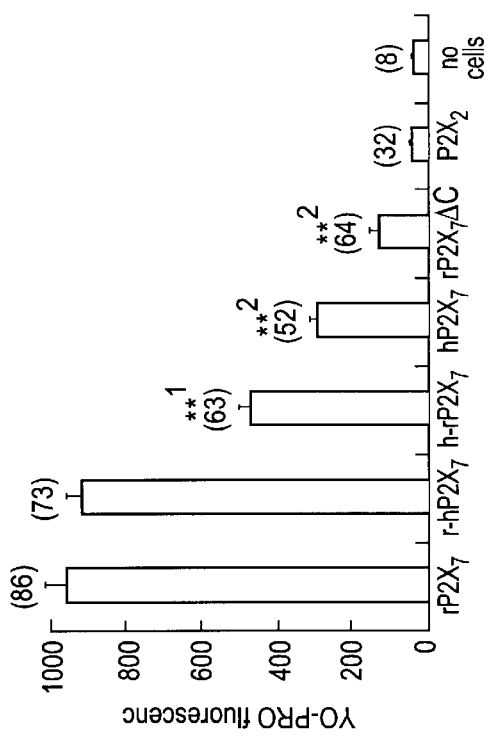
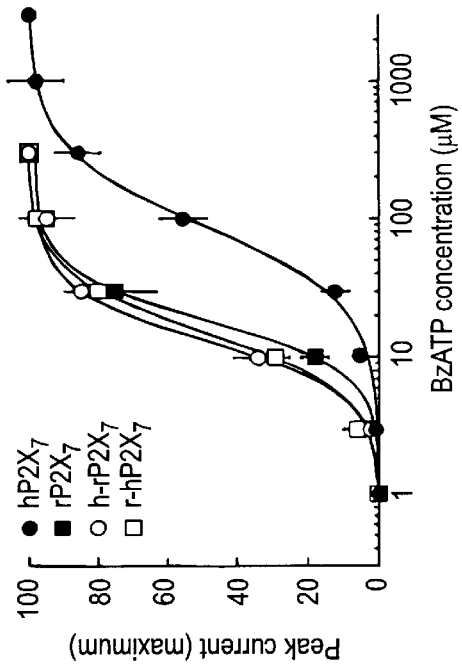
Figure 8A
Figure 8B
Figure 8C

METHODS OF SCREENING MODULATORS OF MAMMALIAN P2X₇ PURINERGIC RECEPTORS

This is a continuation of application Ser. No. 08/842,079, filed Apr. 28, 1997, now U.S. Pat. No. 6,133,434, the entire content of which is hereby incorporated by reference in this application.

TECHNICAL FIELD

The present invention relates, in general, to a purinergic receptor and, in particular, to a $P2X_7$ (also designated P2Z) receptor. The invention further relates to a nucleic acid encoding the $P2X_7$ receptor and to a method of producing $P2X_7$ recombinantly using same. The invention also relates to a method of screening compounds for their ability to inhibit $P2X_7$ activity and thereby for their usefulness in treating a variety of diseases/disorders, including arthritic and respiratory disorders and neurodegenerative diseases.

BACKGROUND

Cell surface receptors for ATP can be divided into metabotropic (P2Y/P2U) and ionotropic (P2X) classes. The metabotropic class belongs to the superfamily of G protein-coupled receptors, with seven transmembrane segments. The ionotropic class members ($P2X_1$-$P2X_6$) are ligand-gated ion channels, currently thought to be multisubunit proteins with two transmembrane domains per subunit (Buell et al, Europ. J. Neurosci. 8:2221 (1996)). P2Z receptors have been distinguished from other P2 receptors in three main ways (Buisman et al, Proc. Natl. Acad. Sci. USA 85:7988 (1988); Cockcroft et al, Nature 279:541 (1979); Steinberg et al, J. Biol. Chem. 262:3118 (1987)). First, activation of P2Z receptors leads not only to an inward ionic current, but also to cell permeabilization. Second, 3'-O-(4-benzoyl)benzoyl ATP (BZATP) is the most effective agonist, and ATP itself is of rather low potency. Third, responses are strongly inhibited by extracellular magnesium ions, which has been interpreted to indicate that $ATP^{4-}$ is the active agonist (DiVirgilio, Immunol. Today 16:524 (1995)).

A seventh member of the P2X receptor family has been isolated from a rat cDNA library and, when expressed in human embryonic kidney (HEK293) cells, exhibits the above three properties (Surprenant et al, Science 272:735 (1996)). This receptor ($rP2X_7$) thus corresponds to the P2Z receptor. $rP2X_7$ is structurally related to other members of the P2X family but it has a longer cytoplasmic C-terminus domain (there is 35–40% amino acid identity in the region of homology, but the C-terminus is 239 amino acids long in the $rP2X_7$ receptor compared with 27–20 amino acids in the others). The $rP2X_7$ receptor functions both as a channel permeable to small cations and as a cytolytic pore. Brief applications of ATP (1–2s) transiently open the channel, as is the case of other P2X receptors. Repeated or prolonged applications of agonist cause cell permeabilization (which permeabilization involves the cytoplasm C-terminus); reducing the extracellular magnesium concentration potentiates this effect.

The P2Z receptor has been implicated in lysis of antigen-presenting cells by cytotoxic T lymphocytes, in the mitogenic stimulation of human T lymphocytes, as well as in the formation of multinucleated giant cells (Blanchard et al, Blood 85:3173 (1995); Falzoni et al, J. Clin. Invest. 95:1207 (1995); Baricolrdi et al, Blood 87:682 (1996)). However, the interpretation of the physiological role of $P2X_7$ receptor has been complicated by functional differences which seem to exist between rodent and man (Hickman et al, Blood 84:2452 (1994)). The human macrophage $P2X_7$ receptor ($hP2X_7$) has now been cloned and its functional properties determined (Rassendren et al, J. Biol. Chem. 272:5482 (1997)).

SUMMARY OF THE INVENTION

The present invention relates to a $P2X_7$ receptor and to a nucleic acid encoding same. The invention also relates to a method of producing $P2X_7$ recombinantly and to a method of screening compounds for their ability to inhibit $P2X_7$ activity. Compounds selected using the present screen can be used to treat a variety of physiological diseases and disorders.

Objects and advantages of the present invention will be clear from the description that follows.

BRIEF DESCRIPTION OF THE DRAWINGS

FIGS. 1A–E. (A) Predicted amino acid sequence of the $P2X_7$ (P2Z) receptor, aligned with that of the $P2X_2$ receptor. The middle line shows common amino acids lines over the top sequence indicate probable membrane-spanning domains, and the square indicates the position of truncation. (B) Rat $P2X_7$ encoding sequence. (C) ATP-induced currents in $P2X_7$ expressing HEK 293 cells are enhanced and prolonged by removal of magnesium. Currents were in response to 1-s applications of ATP (300 $\mu$M, left) and BzATP (right); the smaller of the two responses is in normal solution and the larger is in zero magnesium solution. (D) BzATP-induced currents in J774 cells; solutions with low concentrations of divalent cations also increased both amplitude and duration of the current. (E) BzATP-induced currents in HEK cells expressing $P2X_7\Delta C$; the low divalent solution increased the amplitude but not the duration of the currents. Current amplitude (mean±SEM) to BzATP in normal solution from HEK cells transiently transfected with $P2X_7$ or $P2X_7\Delta C$ was 636±118 pA and 590±95 pA (n=18), respectively. All recordings were from a holding potential of −70 mV; BzATP concentration was 30 $\mu$M in (C) through (E).

FIGS. 2A–F. Pharmacological properties of $P2X_7$ receptors. J774 macrophage cells, and $P2X_7\Delta C$ receptors. (A) Concentration-response curves for ATP (open symbols) and BZATP (closed symbols) in normal (squares) and low divalent (circles) external solution; results are plotted as the percent maximum response to BzATP in normal solution. (B) Concentration-response curves for ATP and ATP analogs (as indicated) in low divalent solution obtained from cells expressing the $P2X_7$ receptor. (C and D) Similar experiments on J774 cells; low divalent solutions also increased both amplitude and duration of the current. (E and F) Similar experiments on HEK cells expressing $P2X_7\Delta C$; all results were from a holding potential of −70 mV.

FIGS. 3A–G. At $P2X_7$ receptors, ATP activates currents that show selectively for small cations (A through C) and also induces a sustained nonselective conductance [(D) through (G)]. In (A), superimposed currents are shown in response to 1-s application of BzATP at the holding potentials indicated (10-mV increments); normal external solution and internal solution contained cesium-aspartate. In (B) were similar experiments on HEK cells expressing the $P2X_7\Delta C$ receptor. Currents were evoked by BZATP at the holding potentials indicated (5-mV increments) in low external divalent solution containing 145 mM NaCl (top) or 145 mM NMDG (bottom). In (C), permeability ratios ($P_K/P_{Na}$) for some monovalent organic cations are plotted with their mean geometric diameter (Murgia et al, J. Biol. Chem.

Figure 1E:
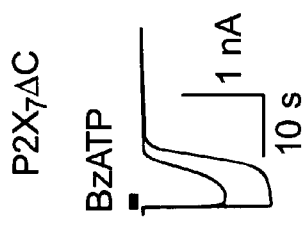

268:8199 (1993)); data were derived from reversal potentials determined as shown in (A), (B), and (G). Filled symbols are for P2X$_7$ receptors (●) and J774 cells (▲) in normal solutions and for P2X$_7$ΔC(♦) and P2X$_2$ (▼) receptors in low divalent solutions. Open circles are for P2X$_7$ receptors in low divalent solutions. (D through G) Repeated application of BZATP induced a sustained nonselective conductance. In (D), currents were recorded from HEK cells expressing P2X$_7$ receptor in response to four 1-s applications of BzATP, with an interval of 12 min between applications in low divalent solution throughout. In (E) is a summary from experiments as illustrated in (D); points are means±SEM (n=6) exponential fits to the offset of the response, with a single exponential for P2X$_7$ΔC(♦) and P2X$_2$ (●) and a double exponential for P2X$_7$ (■). Filled symbols indicate normal concentrations of divalent cations; open symbols, low concentrations. In (F), maintained inward current was evoked by BzATP for 4 s. This application followed four prior applications; low divalent concentration was used throughout. The bar indicates the time during which the superfusing solution was changed from 145 mM NaCl to 145 mM NMDG (still in low concentrations of divalent cations). The arrow indicates the restoration of normal external solution. Breaks (1 to 5) indicate times of conductance measurement. In (G), current-voltage plots were obtained by ramp voltage commands at times 1 to 5 in (F). The very large conductance increase and the lack of effect of NMDG on the reversal potential are noteworthy [compare with (B)].

FIGS. 4A–F. Activation of P2X$_7$ receptors, but not of P2X$_7$ΔC receptors, includes a non-selective conductance and cytolysis. Shown are currents in HEK cells expressing P2X$_7$ (A), P2X$_7$ΔC (B), or P2X$_2$ (C) receptors during repeated applications (1-s each) of BzATP at 100-s intervals. During the time indicated, the external solution was changed from the normal solution to the low divalent solution. The concentration of BZATP was 30 μM in (A) and 300 μM in (B) and (C). YO-PRO-1 could be seen to enter the cell in low divalent solutions during recordings such as that shown in (A)(n=8) but not during experiments as in (B) and (C) (n=7). (D) Photomicrographs of HEK cells stably expressing P2X$_7$ (left) or P2X$_2$ (right) receptors after a 5-min incubation with YO-PRO-1 (10 μM) and BZATP (30 and 300 μM, respectively) in low divalent solution. (E) Summary of results from HEK cells stably expressing P2X$_7$ or PX2$_2$ receptors. (F) Summary of results from cells transiently expressing P2X$_7$, P2X$_7$ΔC, P2X$_2$, or no receptors (Untrans.). BzATP concentration was 30 μM for experiments with the P2X$_7$ receptor and 300 μM for all others (n=5 throughout).

FIGS. 5A–C. Amino acid sequence, encoding sequence, and tissue distribution of hP2X$_7$ receptor. (A) Predicted amino acid sequence of hP2X$_7$ receptor (bottom) aligned with rP2X$_7$ receptor (top). Overlines indicate hydrophobic, putative transmembrane domains and asterisks indicate the positions of amino acid differences. The arrow indicates the exchange point used in the human/rat chimeras. (B) hP2X$_7$ encoding sequence. (C) Tissue distribution of P2X$_7$ mRNA. Size markers (kb) are from an RNA ladder (BRL, Bethesda).

FIGS. 6A–H. ATP-activated currents in HEK293 cells expressing hP2X$_7$ receptors and in human macrophages. (A–C) Expressed hP2X$_7$. (D–F) Macrophagaes. (A and D) Superimposed currents evoked by BZATP (2 s application) in solution containing 2 mM CaCl$_2$ and 1 mM MgCl$_2$ (normal divalents) and after changing to a solution containing 0.3 mM CaCl$_2$ and no magnesium (low divalents). (B) Recordings from one cell in response to application of near maximum concentrations of BzATP or ATP as indicated. (C and F) Currents evoked by BzATP (μM) at different holding potentials (−90 to 30 mV at 20 mV intervals in C and −60 to 60 mV at 30 mV intervals in F). Reversal potentials were near 0 mV in both cases. (E) Superimposed current traces obtained from one macrophage in response to applications of BZATP (300 μM) before, during and after washout of suramin as indicated. Bars above traces indicate duration of agonist application; holding potential was −70 mV in all except C and F. All recordings obtained in low divalent external solution except where indicated in A and D. (G) Inhibition of P2X$_7$ receptor currents by magnesium. Currents evoked by BzATP (30 μM for rP2X$_7$, 300 μM for others; percentage of their value in 1 mM magnesium) as a function of extracellular magnesium concentration. Filled circles are hP2X$_7$, open circles are human macrophage and filled squares are rP2X$_7$; n=3–5 for each point. (H) Concentration-response curves for BzATP-induced currents, in low divalent external solution, n=3–12 for each point.

Figure 7A:
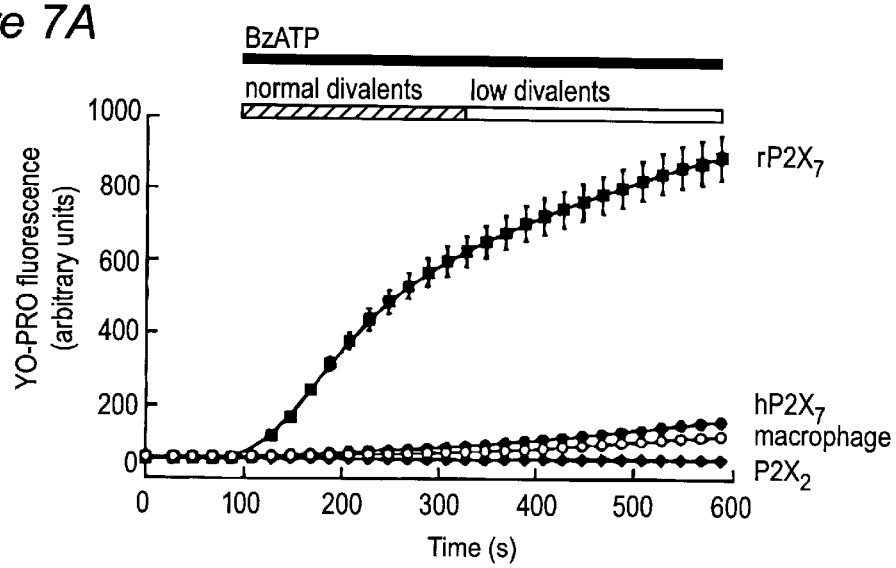
Figure 7B:
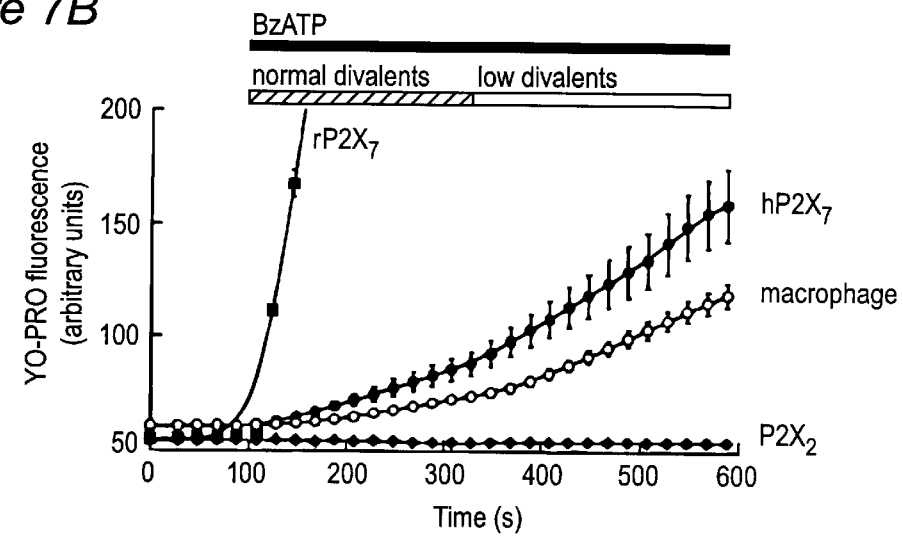
Figure 7C:
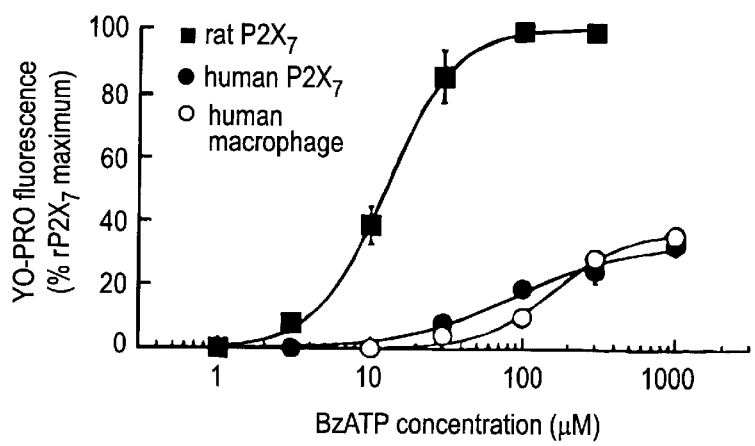

FIGS. 7A–C. YO-PRO-1 uptake in cells expressing P2X$_7$ receptors and in macrophages. (A and B) Time course of YO-PRO-1 uptake and fluorescence. YO-PRO fluorescence (arbitrary units) from HEK293 cells expressing rP2X7 receptors (n=13 cells), hP2X$_7$ receptors (n=12 cells), rP2X$_2$ receptors (n=4 cells) or from human macrophage (n=9 cells) in response to BZATP (100 μM). BZATP was added at time 100 s; the solution was changed from 2 mM CaCl$_2$/1 M MgCl$_2$ to 0.3 mM CaCl$_2$/0 mM MgCl$_2$ at time 300 s ATP (3 mM which is 500-fold greater than EC$_{50}$ value) was used in the case of cells expressing P2X$_2$ receptor. The points show the mean fluorescence (±s.e. mean) for the number of cells indicated. (B) The same data with a expanded ordinate shows more clearly the YO-PRO-1 uptake hP2X$_7$-expressing cells and macrophages. (C) Summary of all results from experiments as in A. Results are expressed as % of maximum YO-PRO fluoresence obtained in rP2X$_7$-expressing cells; each point is average of 6–16 cells from each of 4–6 separate experiments. Points are values measured after 5 min of BZATP application in low divalent external solution.

FIGS. 8A–C. Chimeric human-rat P2X$_7$ receptors. (A) Superimposed traces of currents evoked by BZATP (2 s application, concentrations indicated) in HEK293 cells transfected with hP2X$_7$, h-rP2X$_7$, r-hP2X$_7$ and rP2X$_7$ receptors. Numbers refer to sequential responses recorded during applications at 3–5 min intervals. (B) Concentration-response curves recorded in normal divalent solution for hP2X$_7$ (filled circles), h-rP2X$_7$ (open squares), r-hP2X$_7$ (filled squares) and rP2X$_7$ (open circles) receptors; each point is mean±sem of 3–8 cells. (C) YO-PRO fluorescence evoked by BzATP in HEK293 cells transfected with wild-type rat receptors (rP2X$_7$), chimeric receptors (r-hP2X$_7$ and h-rP2X$_7$), wildtype human receptors (hP2X$_7$), truncated rat receptors (rP2X$_7$ΔC) and P2X$_2$ receptors. The concentration of BZATP was 100 μM, except for hP2X$_7$ (300 μM BzATP) and P2X$_2$ (300 μM ATP). Numbers in parentheses refer to total number of cells measured from 3–6 separate experiments.

Figure 9:
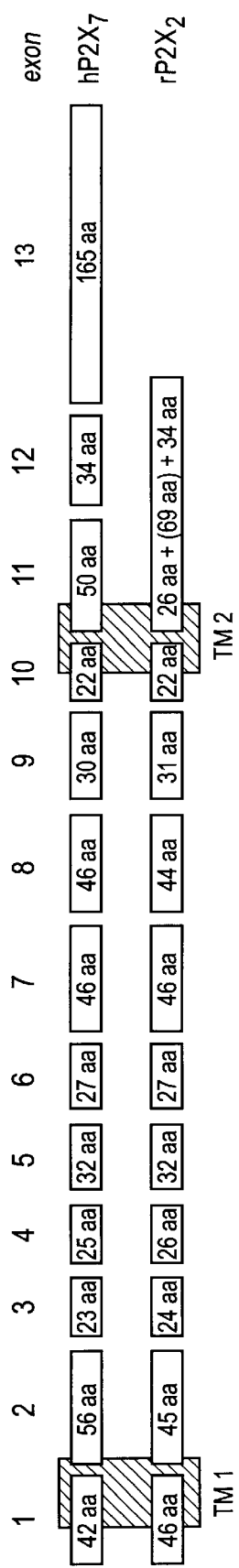

FIG. 9. Schematic comparison of the genes for human P2X$_7$ and rat P2X$_2$ receptors. Boxes represent exons and display the number of encoded amino acids. The two likely transmembrane regions are indicated by shaded regions indicated as TM1 and TM2. Alternative splicing of the rat P2X$_2$ gene has shown that exon 11 may actually consist of two exons of 26 and 34 amino acids, respectively, which are separated by 207 base pairs.

DETAILED DESCRIPTION OF THE INVENTION

The present invention relates to a P2X$_7$ receptor, preferably, a mammalian P2X$_7$ receptor. The present receptor operates both as an ion channel selective for small cations and as an inducer of cell lysis.

The tissue distribution of the $P2X_7$ receptor to which the invention relates has been examined using in situ hybridization and immunohistochemistry. Northern blotting of rat and mouse tissue and cells reveals a 6 kb RNA in newborn but not adult brain. In situ hybridization and immunohistochemistry show heavy expression in the ependyma of newborn and adult brain; the brain parenchyma show no detectable expression (except for regions around areas of necrosis present after occlusion of the middle cerebral artery). NTW8 cells, a mouse microglial cell line, strongly express the $P2X_7$ receptor mRNA and protein. Most bone marrow cells are positive by hybridization and also immunoreactive; this is observed also for marrow cells identified by their expression of other antigens as granulocytes, monocytes and B lymphocytes.

The present invention relates, in one embodiment, to the $P2X_7$ protein, both in its entirety (for example, the FIG. 1A or FIG. 5A sequence, or allelic variations thereof), and to portions thereof as well (and to glycosylated and non-glycosylated forms thereof). The term "portions" relates to peptides and polypeptides of at least 6 or at least 10 or at least 15 amino acids in length, preferably, at least 25, at least 50, at least 100 or at least 300 amino acids. Examples of such fragments include truncated forms of the protein described in the Examples that follow (eg, $rP2X_7$ or $hP2X_7$ truncated at amino acid 418). Advantageously, portions include the N-terminus of the sequence of FIG. 1A or FIG. 5A. Portions corresponding to the C-terminal region of the $P2X_7$ receptor that are responsible, at least in part, for the permeabilizing property of the receptor are also with the scope of the invention (eg from residue 418 to 595 of $rP2X_7$ or $hP2X_7$ receptors).

The present invention also includes proteins having at least 45%, 50%, 60%, 70%, 80%, 90%, 95% or 99% homology with the FIG. 1A and FIG. 5A proteins, in increasing order of preference. One method of determining sequence homology is disclosed in Pearson et al, Proc. Natl. Acad. Sci. USA 85:2444 (1988).

In addition to the $P2X_7$ protein, the present invention also relates to a nucleic acid sequence (DNA or RNA) encoding the receptor, or homolog thereof as described above, and to fragments thereof suitable for use, for example, as probes or primers, of at least 18, preferably at least 30, more preferably at least 75, 150, 300, or 900 bases in length, that encode the "portions" described above. In a specific embodiment, the invention relates to a nucleic acid sequence encoding the FIG. 1A or FIG. 5A amino acid sequence, and portions thereof. In particular, the present invention relates to the FIG. 1B or FIG. 5B nucleic acid sequence or fragments thereof. The nucleic acid can be present in isolated form, for example, free of nucleic acids with which it is normally associated. The present invention also relates to a nucleic acid sequence substantially identical to the nucleic acid sequence of FIGS. 1B or 5B. A "substantially identical" sequence is one the complement of which hybridizes to the nucleic acid sequence of FIG. 1B or FIG. 5B in conditions of high stringency (eg, 0.03M salt (eg NaCl) at 60° C.). (For details of reagent preparation, etc, see Sambrook et al, Molecular Cloning, A Laboratory Manual, 2nd Edition). The invention also relates to nucleic acids complementary to those described above and to nucleic acids at least 60%, 70%, 80%, 90%, 95% or 99% homologous with the FIGS. 1B or 5B sequence.

It will be appreciated from a reading of the Examples that follow that cloning of the $P2X_7$ receptor was complicated by at least two factors. First, the receptor was isolated in two parts, from two distinct tissues. A cDNA encoding the 3' portion was isolated from a rat superior cervical ganglion cell library; this overlapped with a cDNA encoding the 5' portion which was isolated from a library made from a rat brain region (the habenula). The two pieces were then joined, and a full length cDNA later identified. Second, the recognition of the novel, cell permeabilizing, properties of this receptor was unexpected. When the receptor was expressed in heterologous cells, electrophysiological recording was used to study its channel properties. In the course of these recordings, some unique properties of the $P2X_7$ receptor were noticed (low sensitivity to ATP compared with 2' and 3'-O-(benzoyl)-4-benzoyl-ATP, and marked potentiation by reducing the external calcium and magnesium concentrations); this led to the receptor being tested for the cell permeabilizing function.

The present invention also relates to a recombinant molecule (a construct) comprising a nucleic acid sequence as described above and to a host cell transformed therewith. Using methodologies well known in the art, a recombinant molecule comprising a vector and a nucleic acid sequence encoding a $P2X_7$ receptor of the invention, or portion thereof as defined above, can be constructed. Vectors suitable for use in the present invention include plasmid vectors (eg, pcDNA and others containing, for example, mammalian promoters) and viral vectors (eg, Semliki forest virus, baculovirus, adenovirus, vaccinia virus, etc). Appropriate vectors can be selected based on their compatibility with transformation into a selected host cell. The nucleotide sequence of the invention can be present in the vector operably linked to regulatory elements, for example, a promoter. Suitable promoters include, but are not limited to the cytomegalovirus, SV40 and polyhedral promoters.

As indicated above, the recombinant molecule of the invention can be constructed so as to be suitable for transforming a host cell. Suitable host cells include prokaryotic cells, such as bacteria, particularly *E. coli*, lower eukaryotic cells, such as yeast or pichia, and higher eukaryotic cells, such as insect or mammalian cells. The recombinant molecule of the invention can be introduced into appropriate host cells using a variety of known methods.

The present invention further relates to a method of producing the $P2X_7$ receptor of the invention, or portions thereof as defined above. The method comprises culturing the above-described transformed host cells under conditions such that the encoding sequence is expressed and the protein thereby produced. The protein can be isolated by epitope-tagging and affinity purification.

The $P2X_7$ receptor of the invention, or portions thereof as defined above, can be present in isolated form, for example, substantially free of proteins with which it is normally associated. Advantageously, the protein is at least 90% pure, more preferably at least 99% pure (as determined, for example, by gel electrophoresis). The proteins, polypeptides and peptides of the invention can be produced recombinantly using the nucleic acid sequences as described above, or chemically using known methods. When prepared recombinantly, the protein of the invention can be produced alone or as a fusion product, for example, fused with a protein such as glutathione S-transferase. For example, the coding sequence of the invention (eg a sequence encoding the amino acid sequence of FIGS. 1A or 5A) can be cloned in frame with a sequence encoding another protein (such as glutathione S-transferase) and the fusion product expressed in an appropriate host cell.

The proteins, polypeptides and peptides of the invention can be used as antigens to generate $P2X_7$ specific antibodies.

Methods of antibody generation are well known in the art. Both monoclonal and polyclonal antibodies are contemplated, as are antigen binding fragments thereof. Such antibodies can be used, for example, to effect purification of $P2X_7$ (eg via affinity chromatography) or to detect the presence of $P2X_7$ in biological samples, including tissue and cell samples (eg using immunohistochemical approaches).

The $P2X_7$ receptor can be used as a screen for compounds useful in a variety of mammalian (human and non-human) diseases and conditions. In one embodiment of such a screen, a host cell transformed with a $P2X7_2$ encoding sequence is contacted with an agonist, for example, ATP or BzATP, in the presence and absence of a test compound. The effect of the test compound on the activation of the receptor is then determined, for example, using the ion current measurements and cell permeabilization measurements described in the Examples that follow. Compounds that inhibit receptor activation are likely to be of value in disorders of the nervous system (particularly those diseases with a component of chronic inflammation, such as Alzheimer's disease), diseases involving acute or chronic inflammation (including but not limited to rheumatoid arthritis, amyloidosis, bacterial, viral and other microbial infections), and disorders of the hematopoietic system and immune response (including but not limited to autoimmune disorders, allergies and lymphoproliferative disorders), and diseases involving apoptotic cell death, such as cardiac and cerebral ischemia. Compounds that activate $P2X_7$ receptors are likely to be of value in microbial infections, particularly tuberculosis.

Compounds selected using the above-described screen can be formulated as pharmaceutical compositions using known methods. Appropriate administration regimens can be established by one skilled in the art.

The structure of the $P2X_7$ gene is shown in FIG. 9 (the human $P2X_7$ gene has been localized to chromosome 12q24). The availability of this structure makes possible the construction of disrupted genes and thus the creation of transgenic animals, including a $P2X_7$ receptor gene knockout mice. Such animals can be expected to be of importance in drug screening and furthering the understanding of the function of purinergic receptors.

Certain aspects of the present invention are described in greater detail in the non-limiting Examples that follow.

EXAMPLE 1

Isolation of a P2Z ($P2X_7$) Receptor cDNA

Experimental Details

A 440-base pair (bp) fragment of $P2X_7$ was amplified with inosine-containing degenerate oligonucleotides from several peripheral autonomic ganglia (Buell et al, EMBO J. 15:55 (1996)). Using this fragment as a hybridization probe, a partial $P2X_7$ cDNA was isolated from λgt10 prepared from rat superior cervical ganglia mRNA. This 3.5-kb cDNA was truncated at the 5' end, beginning with the codon for amino acid residue 141, and did not have a polyadenylated [poly$(A)^+$] tail. An additional 468 bp of 5' cDNA was cloned by rapid amplification of cDNA ends-polymerase chain reaction (RACE-PCR; Life Technologies, Bethesda, MD) using poly$(A)^+$ RNA from the medial habenula. $P2X_7$ receptor-specific sequences were amplified with two rounds of nested PCR, for which sense primers were CCACGCGTCGAC-TAGTACGGGIIGGGIIGGGIIG and GGAATTC-CACGCGTCGACTAGTAC and antisense primers were GGCGTATCTGAAGTTGTAGC and GTCCAGCCGGCG-GAAGCTGT. A shared restriction site (Bgl II) permitted ligation of the RACE-PCR product and of the partial cDNA, yielding a construct that encoded the entire $P2X_7$ protein. This chimera (GenBank accession number X95882) was expressed in pcDNA3 (Invitrogen, San Diego, Calif.), sequenced by fluorescent DNA sequencing (Perkin Elmer, Foster City, Calif.), and confirmed by isolation of other full-length $P2X_7$ cDNAs from a rat brain cDNA library (Clontech, Palo Alto, Calif.). One of these included a stop codon 130 bp upstream from the ATG. The COOH-terminus was removed by excision of a Xcm I-Not I fragment, and the resulting protein ($P2X_7\Delta C$) was $P2X_7$ (1–418).

Digoxigenin-labeled antisense riboprobe was generated from the full-length $P2X_7$ cDNA and used for Northern (DNA) blotting on 300 ng of poly$(A)^+$ RNA of each sample that had been electrophoresed and transferred to nylon; hybridization was detected by chemiluminescence.

Results

A P2X receptor complementary DNA (cDNA) ($P2X_7$) was isolated that encodes a 595-amino acid protein (FIG. 1A). The first 395 amino acids were 35 to 40% identical to those of the other six P2X receptors, which are thought to have short intracellular $NH_2$— and COOH-termini, two transmembrane domains, and a large extracellular loop (Suprenant et al, Trends Neurosci. 18:224 (1995)). The COOH-terminal domain of the $P2X_7$-receptor was much longer than that found in the other receptors but contained no further hydrophobic region that might span the membrane and showed no sequence homology with known proteins. The mRNA for the $P2X_7$ receptor was strongly expressed in J774 and P815 macrophages, in microglia, brain, spinal cord, lung, and spleen but was absent from thymus or the granulocytic RBL cell line.

EXAMPLE 2

Pharmacological Profile of P2Z Receptor

Experimental Details

Whole-cell recordings were obtained at room temperature from HEK293 cells transiently or stably transfected with $P2X_7$ cDNA, from HEK293 cells transiently transfected with $P2X_7\Delta C$ cDNA, and from J774A.1 cells (American Type Culture Collection, Rockville, Md.). Agonist were applied for periods of 1 to 3 s by a fast-flow U-tube delivery system (Fenwick et al, J. Physiol. (London) 331:577 (1982)). The internal pipette solution was 140 mM cesium-aspartate or potassium-aspartate, 20 mM NaCl, 10 mM EGTA, and 5 mM Hepes: normal external solution was 145 mM NaCl, 2 mM KCl, 2 mM $CaCl_2$, 1 mM $MgCl_2$, 10 mM Hepes, and 12 mM glucose. Low divalent external solution was nominally magnesium-free with 0.3 mM $CaCl_2$. For cells expressing $P2X_7$ receptors and J774 cells, concentration-response curves were constructed in low divalent solution by recording currents in response to 1-s applications of agonist at 8-min intervals with normal external solution present for 6 min before each application. This protocol was necessary to prevent the development of sustained inward currents. Lipofectin was used for transfection (Buell et al, EMBO J. 15:55 (1996)).

Reversal potentals ($E_{rev}$) were obtained by application of ATP (300 μM) or BzATP (30 μM) while the membrane was held at various potentals or by application of voltage ramps from −120 to 30 or 50 mV. Permeability ratios from ($E_{rev}$) were calculated by first computing α (=$P_{na}/P_K$, where P is permeability) for internal (i) and external (o) concentrations $[Na]_i$=20 mM, $[Na]_o$=145 mM, $[K]_o$=0 mM, and $[K]_i$=140 mM from α={[145/exp($E_{rev}$)F/RT −20]}/140 (where F is the Faraday, R is the gas constant, and T is the absolute temperature). Other $P_K/P_{Na}$ values, when $[X]_o$=145 mM, $[Na]_i$=20 mM, $[K]_i$=140 mM, and $[Na]_o$=$[K]_o$=$[X]_i$=0 mM, were computed from $P_K/P_{Na}$={[exp ($E_{rev}$F/RT) (20=140α)]}/145. In order of size (FIG. 3C), X was cesium, methylamine, tris(hydroxymethyl)-aminomethane, tetraethylammonium, and N-methyl-D-glucamine. The internal solution also contained 10 mM EGTA and 5 mM Hepes. External solutions also contained 10 mM glucose and normal or low concentrations of divalent cations; pH was maintained at 7.3 with HCl, histidine, or Hepes as required, and the osmolarity of all solutions was 295 to 315.

YO-PRO-1 (10 μM; Molecular Probes, Eugene, Oreg.) was added to the superfusion fluid during electrophysiological recordings 3 to 6 min before switching to low divalent solution and washed out upon switching back to normal divalent solution, after which the fluorescent lamp was turned on and cells were examined with a fluorescein isothiocyanate filter. For cell counts, 500 cells per cover slip were counted in each case.

Results

Figure 1D:
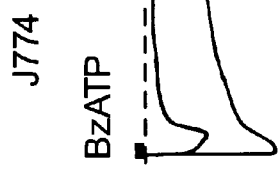
Figure 1C:
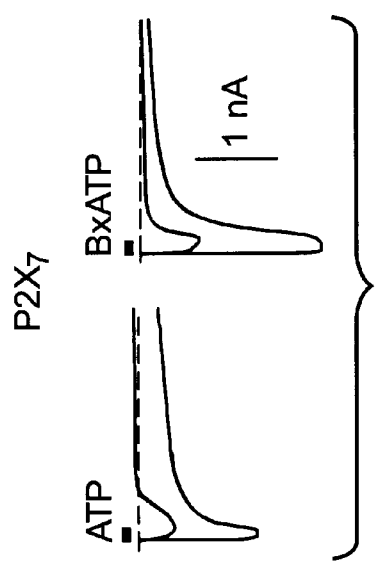

Brief application (0.5 to 2s) of ATP evoked inward currents in HEK293 cells into which the $P2X_7$ receptor was transiently or stably transfected (see FIG. 1C). The agonist order of potency was BzATP>>ATP>2MeSATP>ATP-γ-S>>ADP (FIGS. 2, A and E) [where Bz is 2' and 3'-(O)-(4-benzoyl benzoyl) and Me is methyl]; αβ-methylene ATP, βγ-methylene ATP, UTP, and adenosine were ineffective (concentration, 300 to 1000 μM). The removal of magnesium, calcium, or both from the external solution increased the amplitude of the current (FIGS. 1C and 2A) and greatly prolonged the current, particularly when the applications were repeated. The increase in peak current (1.5- to 8-fold) was associated with little change in the half-maximal concentration ($EC_{50}$) (it has been suggested that $ATP^{4-}$ is the active species at the P2Z receptor (Nuttle et al, J. Biol. Chem. 269:1398 (1994)). The three solutions used contained 2 mM $CaCl_2$ and 1 mM $MgCl_2$, 2 mM $CaCl_2$ and 0 mM $MgCl_2$ and 0.3 mM $CaCl_2$ and 0 mM $MgCl_2$; the concentrations of $ATP^{4-}$ resulting from the addition of 100 μM Na-ATP to these solutions would be 3.7); values for $EC_{50}$ for BzATP and ATP were 7±2 μM and 115±9 μM in normal solution (n=4) and 3.7±0.7 μM and 85±8 μM in zero magnesium (n=7), respectively.

Currents with the same pharmacological profile were also recorded from J774 cells (FIGS. 1D and 2, C and D). Antagonists had similar effects on J774 cells and HEK cells expressing the $P2X_7$ receptor: currents evoked by 30 μM BzATP were relatively insensitive to the purinoceptor antagonist suramin (15 to 38% inhibition with a concentration of 300 μM, n=5) and moderately sensitive to the P2X antagonist pyridoxalphosphate-6-azophenyl-2',4'-disulfonic acid (half-maximal inhibition, 45±8 μM in four HEK cells and 60±9 μM in three J774 cells). Oxidized ATP (Murgia et al, J. Biol. Chem. 268:8199 (1993)) (100 μM) irreversibly blocked currents, provided cells were preincubated for 1 to 2 hours (n=5); hexamethylene amiloride, which blocks the large pore formation at some P2Z receptors (Nuttle et al, J. Biol. Chem. 269:13988 (1994)), was ineffective (100 μM, n=6) at blocking current. The $P2X_7$ receptor thus presents a pharmacological profile typical of the receptor previously termed P2Z (Buisman et al, Proc. Natl. Acad. Sci. USA 85:7988 (1988); Zambon et al, Cell Immunol. 156:458 (1994); Nuttle et al, J. Biol. Chem. 269:13988 (1994); Blanchard et al, Blood 85:3173 (1995); DiVirgilo et al, Immunol. Today 11:247 (1990); Liu et al, Immunol. Today 16:194 (1995)).

Figure 3G:
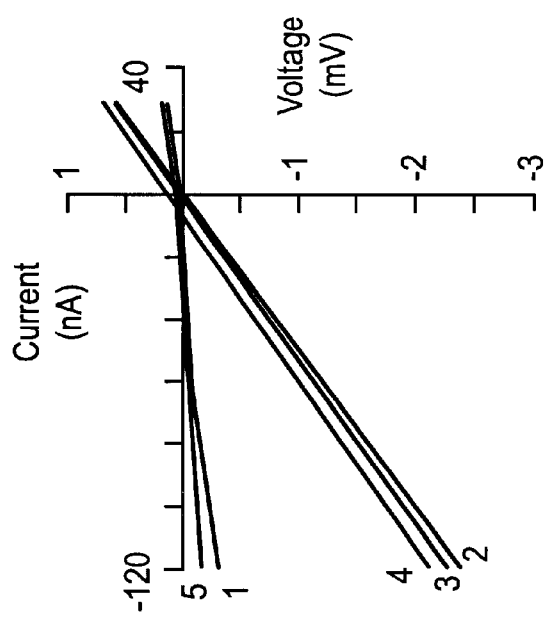

The BzATP-induced currents reversed polarity at −2±0.3 mV (n=4); unlike currents at other P2X receptors (Collo et al, J. Neurosci. 16:2495 (1996); Brake et al, Nature 371:519 (1994); Valera et al, Nature 371:516 (1994); Chen et al, Nature 377:428 (1995); Lewis et al, Nature 377:432 (1995); Buell et al, EMBO J. 15:55 (1996)), they showed no rectification between −90 and 50 mV (FIG. 3A) . The relative permeabilities of monovalent organic cations in the presence of external divalent cations were the same for $P2X_7$ receptors expressed in HEK cells and native J774 cells and were not significantly different from those found previously for $P2X_2$ receptors (Evans, J. Physiol. (London) 487:193P (1995)) (FIG. 3C); the large cation N-methyl-D-glucamine (NMDGA) was not significantly permeable (FIG. 3C). Reduction of the concentration of magnesium or calcium increased the current (FIGS. 1C and 2A) but did not change the current-voltage relation, which was approximately linear (n=5).

Figure 3F:
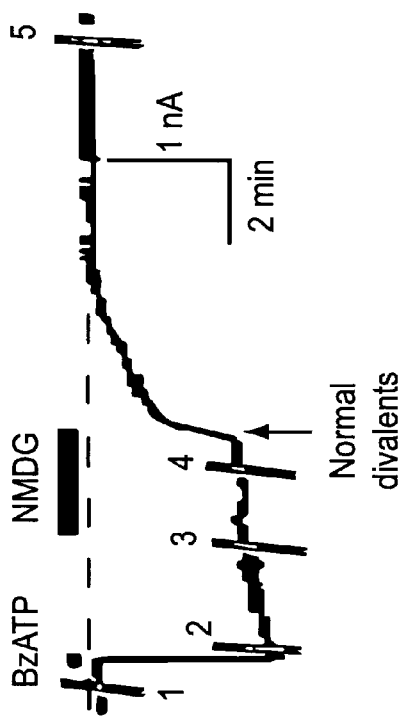
Figure 4A:
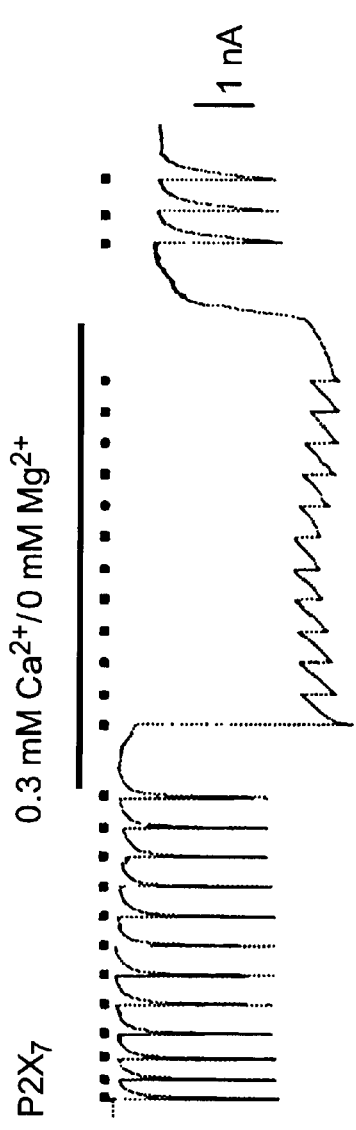
Figure 4B:
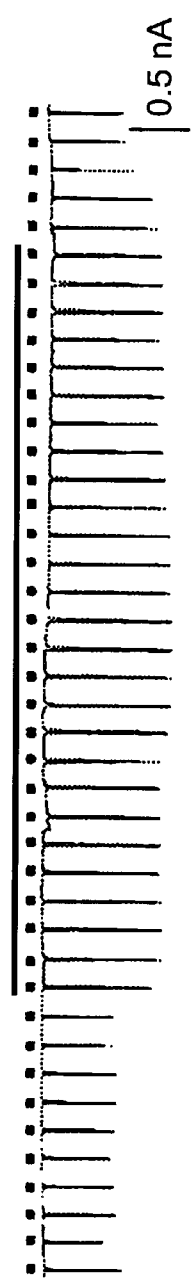
Figure 4C:
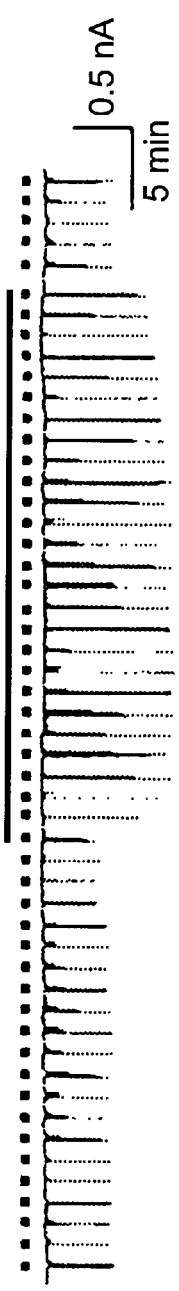
Figure 4D:
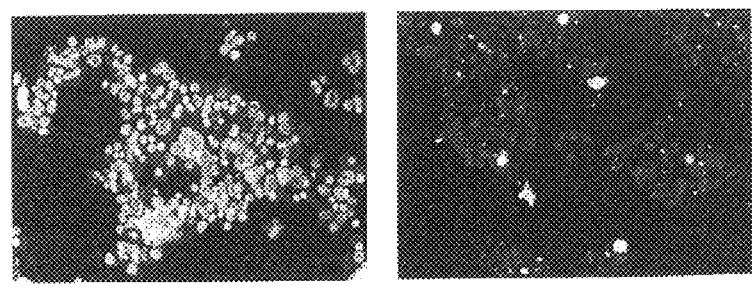
Figure 4E:
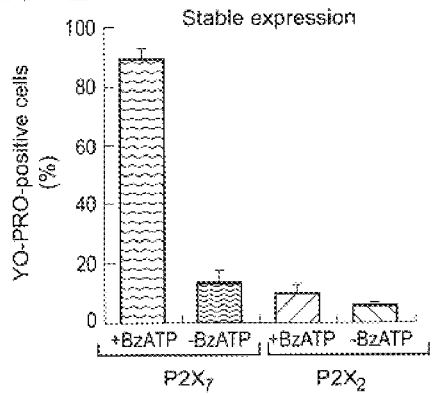
Figure 4F:
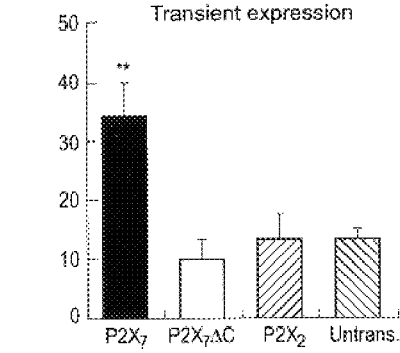

The P2Z receptor has been characterized primarily by ion flux and dye uptake studies in macrophage-derived cell lines such as J774, particularly with the use of BzATP as the agonist and low extracellular divalent ion concentrations (Buisman et al, Proc. Natl. Acad. Sci. USA 85:7988 (1988); Zambon et al, Cell. Immunol. 156:458 (1994); Nuttle et al, J. Biol. Chem. 269:13988 (1994); Wiley et al, Br. J. Pharmacol. 112:946 (1994); Steinberg et al, J. Biol. Chem. 262:8884 (1987); Hickman et al, Blood 84:2452 (1994)). A difference in the action of BzATP was found when the single brief applications were repeated in low concentrations of divalent cations (1 to 3 s duration with 30 μM BzATP at intervals of 2 to 15 min) (FIGS. 3, D and E, and 4A). The currents declined much more slowly after each application, leading to sustained currents (FIGS. 3, D and F) that reversed only very slowly (up to 20 min) when the agonist applications were stopped (the induction and kinetics of this sustained current were the same for inward current at −70 mV and for outward current at 50 mV (n=3)—it did not require any current to flow during the first, conditioning agonist applications: when BzATGP was applied 4 to 12 times in normal divalent solution while the reversal potential was held (0 mV in NaCl or −90 mV in NMDG), the sustained current was still evoked by the subsequent application of BZATP when the low divalent solution was introduced and the holding potential was set to −70 mV (n=3)). However, the currents reversed within 1 to 3 min if the normal divalent cation concentration was restored (FIGS. 3F and 4A). The conductance increase during the sustained current evoked by repeatred applications of ATP (300 μM) or BzATP in a solution with a low concentration of divalent cations was almost nonselective among cations, with the cells becoming very permeable even to NMDG (FIGS. 3, C, F, and G). The large molecular size (629 daltons) propidium dye YO-PRO-1 (Wiley et al, Br. J. Pharmacol. 112:946 (1994); Steinberg et al, J. Biol. Chem. 262:8884 (1987); Hickman et al, Blood 84:2452 (1994)) could be seen to enter the cell during these recordings (FIG. 4A). In separate experiments, it was found that >85% of stably transfected cells took up YO-PRO-1 during incubation with BzATP for 3 to 5 min in a solution with a low concentration of divalent cations (FIGS. 4, D and E).

In normal or reduced concentrations of divalent cations, repeated applications of ATP or BZATP did not induce such sustained currents in cells expressing other P2X receptors (Evans et al, Mol. Pharmacol. 48:178 (1995)) (FIGS. 3E and 4C) and did not cause uptake of YO-PRO-1 by HEK cells expressing the P2X$_7$ receptor (FIGS. 4, D through F). The hypothesis that the unique COOH— terminal domain conferred these preperties was tested by repeating the experiments on HEK cells expressing the P2X$_7$ receptor truncated to 418 amino acids (P2X$_7$ΔC, FIG. 1A). Agonist and antagonist actions at this P2X$_7$ΔC receptor were not different from those at wild-type receptors, and reduction of divalent cations increased the amplitude of the response at P2X$_7$ΔC receptors as at wild-type P2X$_7$ receptors (FIGS. 1D and 2, E and F). However, in cells expressing the P2X$_7$ΔC receptor, solutions with low concentrations of divalent cations did not alter the kinetics of the response, the sustained current was not induced by repeated applications (FIGS. 1E; 3, B, C, and E; and 4B), and no uptake of YO-PRO-1 was induced by BzATP (FIGS. 4, E and F).

EXAMPLE 3

Human P2X$_7$ (P2Z) Receptor Cloning

Experimental Details

Cloning. A 433 bp fragment of the rat P2X$_7$ receptor described in Example 1 was used as a probe to screen at low stringency a λgt10 human monocyte cDNA library from human monocytes (Clontech: 1050a). Phage DNA was prepared from three positive plaques and digested by EcoRl. Fragments were cloned into EcoRI prepared pBluescript (Stratagene) and sequenced by fluorescent sequencing. These three clones encoded partial overlapping cDNAs with high sequence homology to rP2X$_7$. For functional expression, a clone containing the complete open reading frame of the hP2X7 receptor was constructed by overlapping PCR using phage DNA as template. The entire coding sequence was subcloned into the NotI site of pcDNA3 (Invitrogene) using NotI sites included in the amplification primers. All PCR amplified material was confirmed by sequencing. The nucleotide sequence was confirmed by RT-PCR on human mRNA from brain, spleen and from the macrophage cell line U937. The sequence was identical except for the finding of either C or T at position 499, which encodes either His or Tyr at amino acid 155 (Tyr in rP2X$_7$ receptor); this probably reflects allelic variation of the human P2X$_7$ gene because the variation was also found in genomic DNA coming from a single donor.

Northern blot analysis. Multiple tissue Northern blots (Clontech) were hybridized with a 809 bp fragment (1351–2160) generated by PCR amplification and random-primed with $\alpha^{32}$PdCTP. Hybridization was at 42° C. in 50% formamide with final washes with 1×SSC (55° C. for 20 min). Blots were exposed for 4 days at −80° C.

Chimeras. A silent restriction site (NheI) was introduced at the equivalent positions in the rat and human cDNAs using the Pfu mutagenesis kit (Stratagene) (T to G at 1069 in rP2X$_7$; G to A at 1072 in hP2X$_7$). A NheI-XhoI fragment corresponding to 3' extremity of each cDNA was then excised and subcloned in the opposite plasmid (i.e. human 3' end into rat background). The resulting chimeras were h-rP2X$_7$ (human 1–346, rat 347–595) and r-hP2X$_7$ (rat 1–346, human 347–595) (FIG. 5). All constructions were sequenced on their entire coding region.

Cell culture. HEK293 cells were transiently transfected with cDNA (1 μg/ml) and lipofectin dissolved in Optimem (GIBCO) placed into petri dishes containing four coverslips onto which cells were plated at a density of about 8×10$^4$/ coverslip. Cells were washed 5 h later and normal DMEM applied. Electrophysiological studies or dye uptake measurements were carried out 18–49 h later. For each set of transfections, parallel experiments were performed on HEK cells transfected with cDNA encoding both rP2X$_7$ and hP2X$_7$ receptors.

Human macrophages. Monocyte-derived human macrophage cultures were prepared as described by, Blanchard et al (Blanchard et al, J. Cell Biochem. 57:452 (1995); Blanchard et al, J. Immunol. 147:2579 (1991)). Briefly, monocytes were isolated from leukocyte concentrates obtained from a healthy male volunteer. Leukocytes were resuspended in RPMI 1460 medium (GIBCO) with 20% human serum, 2 mM glutamine, 5 mM HEPES and 100 μg/ml streptomycin. Cells were allowed to adhere to culture flasks for 1–2 h, after which non-adherent cells were washed away. Adherent cells were cultured for 7–14 d in this medium plus human interferon-γ (1000 units/ml). Macrophages were recovered from the culture flask by pipetting with cold phosphate-buffered saline, and plated onto glass coverslips for electrophysiological and YO-PRO uptake experiments which were carried out 12–24 h later.

Electrophysiological experiments. Whole-cell recordings were made using the EPC9 patch-clamp amplifier and Pulse acquisition programs (HEKA, Lambrecht, Germany). Patch pipettes (5–7 MΩ) contained (mM) CsCl or NaCl 154, EGTA 10, HEPES 5. The normal extracellular solution contained (mM) NaCg 147, KCl2, CaCl$_2$ 2, MgCl$_2$ 1, HEPES 10 and glucose 12, and the "low divalent" solution had no magnesium and 0.3 mM CaCl$_2$. Agonists were delivered by U-tube delivery system; antagonists, when applied, were present in both superfusion and U-tube. Experiments were carried out at room temperature.

YO-PRO-1 fluorescence. The Photonics Imaging, (IDEA) system for microscopic fluorescence measurements (Photonics, Planegg, Germany) was used. Coverslips were placed on the stage of a Zeiss Axiovert 100 inverted microscope and viewed under oil immersion with a 40x Fluar objective. YO-PRO-1 (Molecular Probes, Eugene Oreg.) fluorescence was measured using 491/509 excitation/ emission wavelengths. Images were obtained at 5–20 s intervals during, continuous superfusion (2 ml/min) with YO-PRO-1 (2 μM) and varying concentrations of ATP or BZATP. For each experiment, the time course of YO-PRO-1 fluorescence was obtained for 10–20 individual cells (eg. FIG. 7A) and then averaged to obtain the mean fluorescence signal. It usually was not possible to follow YO-PRO-1 fluorescence in rP2X$_7$-expressing cells for more than 3–5 min after application of maximum concentrations of BZATP because the extensive cell lysis caused the cells to detach from the coverslip. Therefore, results were expressed as mean signal at 3 min for rP2X$_7$ while signal at 10 min was used for hP2X$_7$ and human macrophage cells. All experiments were carried out at room temperature.

Results

Isolation of hP2X$_7$ CDNA from monocytes. Three phage with overlapping inserts were isolated from a human monocyte library by low stringency hybridization with a rP2X$_7$ probe. The clones spanned a region of 3076 bp encoding an open reading frame of 595 amino acids. (FIG. 5A) This protein is 80% identical with rP2X$_7$ receptor, with no particular regions of the sequence being more related than others; this identity is less than that found for the rat/human comparisons of P2X$_1$, P2X$_3$ and P2X$_4$ receptors (91, 94 and 88% respectively) (hP2X$_1$: Valera et al, Receptors and Channels 3:283 (1995)); hP2X$_4$: Garcia-Guzman et al, Mol. Pharm. 51:109 (1997)).

The cDNA isolated from the monocyte library did not contain a poly(A)+ tail in the 3'-untranslated region, suggesting a larger size for the mature RNA. Northern blotting detected a single band of about 6 kb, with strong signals in pancreas, liver, heart and thymus, and moderate to low levels in brain, skeletal muscle, lung, placenta, leucocytes, testis, prostate and spleen. (FIG. 5C) A similar distribution was seen for the rat P2X$_7$ receptor, and indicates that the P2X$_7$ receptor has a much more widespread distribution than previously considered on the basis of functional responses of the 'P2Z' type.

Figure 6A:
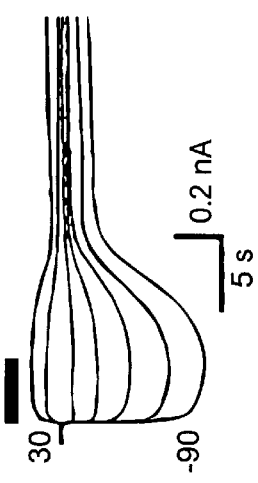

Electrophysiological properties of hP2X$_7$ receptors in HEK293 cells. Brief application (1–3 s) of ATP or BZATP of HEK293 cells transiently transfected with hP2X$_7$ receptors evoked inward currents (at −70 mV) (FIG. 6). The currents were linearly dependent on membrane potential (−90–30 mV) (FIG. 6C) and were carried by cations: reversal potentials in external sodium (154 mM) or potassium (147 mM) were −1±0.2 mV (n=4) and 0.5±0.05 mV (n=3), respectively, and were not significantly altered when internal chloride was replaced with aspartate (n=6). Removal of extracellular magnesium (and/or calcium) greatly enhanced the responses (FIG. 6A). BZATP was 10-fold more potent than ATP to activate the receptor. The currents evoked by BZATP were blocked by relatively high concentrations of suramin and pyridoxal 5-phosphate-6-azophenyl 2'4'-disulfonic acid (PPADS); the concentrations causing half-maximal inhibition were similar to those seen in the rat (for hP2X$_7$: suramin 92±8 $\mu$M (n=4) and PPADS 62±4 $\mu$M (n=4) vs 300 $\mu$M BzATP, and for rP2X$_7$: suramin 78±3 $\mu$M (n=3) and PPADS 51±4 $\mu$M (n=3) vs 30 $\mu$M BzATP). In these respects, the properties of the human receptor resemble those of the rat.

Figure 6B:
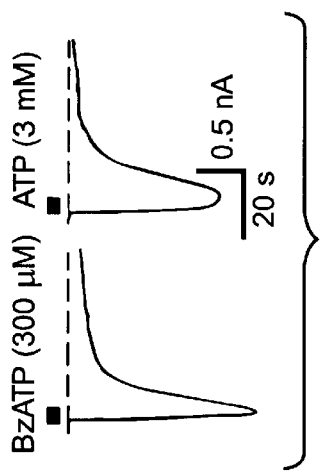
Figure 6C:
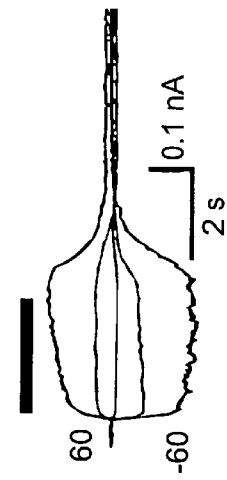
Figure 6D:
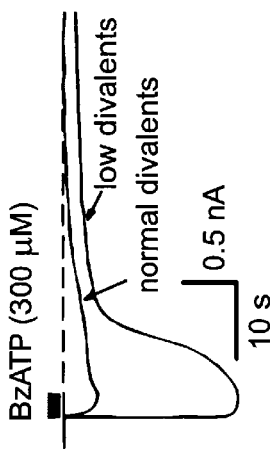
Figure 6E:
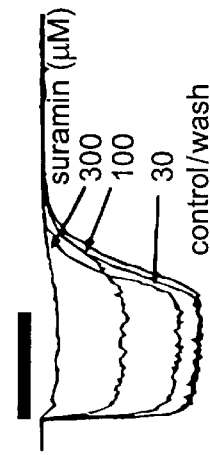
Figure 6F:
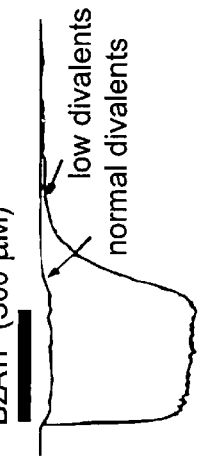
Figure 6H:
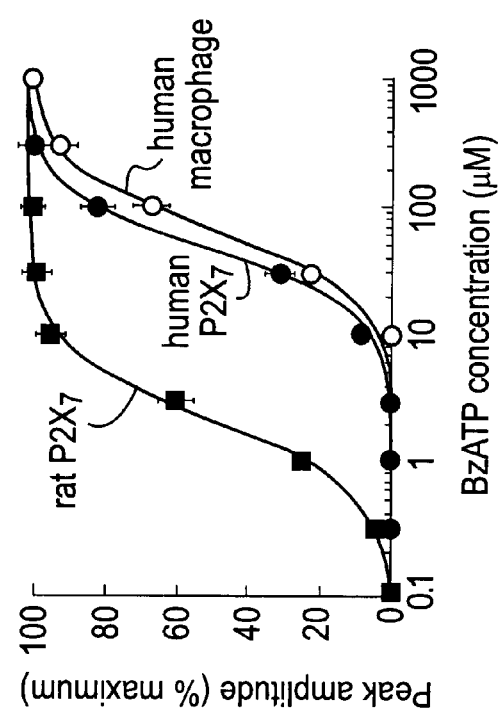
Figure 6G:
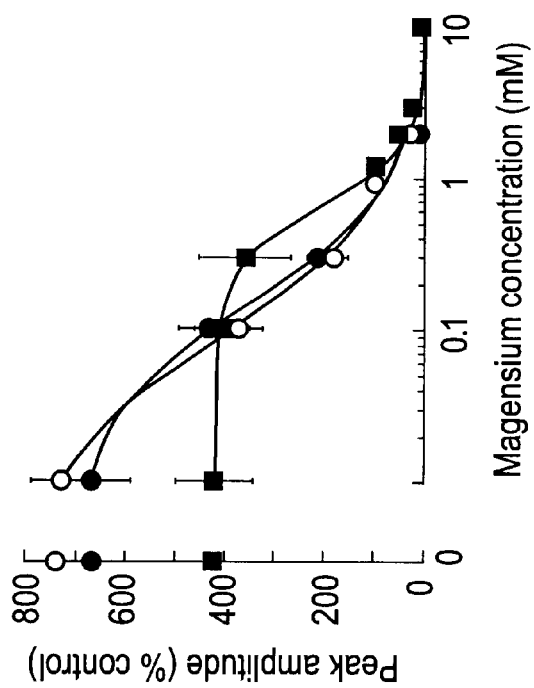

There were also marked differences between hP2X$_7$ and rP2X$_7$ receptors. First, higher concentrations of agonists were required to activate hP2X$_7$ receptors. The half-maximal concentration (EC$_{50}$) of BzATP to activate hP2X$_7$ receptors was 25-fold greater than for the rP2X$_7$ receptor (FIG. 6H) and the ATP EC$_{50}$ value was about 10-fold greater. Second, removal of external magnesium increased the hP2X$_7$ currents to a greater degree than the rP2X$_7$ currents (670±80% vs 420±84%, p<0.05; FIG. 6G); the concentration of magnesium which caused half-maximal inhibition of the current was significantly lower for the hP2X$_7$ receptor (212 $\mu$M vs 780 $\mu$M, p<0.0001). Third, the time courses of the deactivation of the current differed. One of the unusual features of the rP2X$_7$ receptor is that, when the extracellular concentration of divalent cations is reduced, a very prolonged current (up to 10–20 min) is induced by even a very brief agonist application (1–3 s) (see Example 2). This prolonged component has a different underlying ionic basis, for the membrane becomes permeable to large cations (such as N-methyl-D-glucamine) in addition to small cations; it becomes progressively more evident when the agonist applications are repeated (see Example 2). This behavior was much less marked in the case of the hP2X$_7$ receptor. Even repeated applications of BzATP (300 $\mu$M; 20–30 times for 3 s duration at 1 min intervals) in low extracellular divalent concentrations evoked currents which largely declined to baseline within 10–20 s of discontinuing the application. For the hP2X$_7$ receptor, the current measured at 30 s was 18±2% of the peak current (n=16), and the corresponding values for the rP2X$_7$ receptor was 80±3% (n=13). On the other hand, the human receptor did exhibit a slow component to the current deactivation when compared to the rP2X$_2$ receptor; this appeared as a 'tail' in the offset of the response, typically lasted for 1–3 min, and accounted for 8–17% of the total current integral (n=7) (FIGS. 6A–C).

Human macrophage ATP receptors. BzATP or ATP evoked currents in macrophages which resembled closely those observed upon activation of heterologously expressed hP2X$_7$ receptors (FIGS. 6D–H). This was true for inhibition by magnesium (FIG. 6D and G), block by suramin (FIG. 6E), reversal potential (FIG. 6F) and aconist potency (FIG. 6H).

Uptake of YO-PRO-1. A striking property of rP2X$_7$ receptor, when compared to other P2X receptors, is its ability to induce cell lysis; this results from the formation of large pores which are permeable to high molecular weight dyes such as YO-PRO-1 (629 daltons). YO-PRO-1 uptake into cells expressing hP2X$_7$ receptors was therefore measured, and comparative measurements made in human macrophages, cells expressing rP2X$_7$ receptors and cells expressing rP2X$_2$ receptors. FIG. 7A shows the time course of YO-PRO-1 fluorescence from single cells during super-fusion with BzATP, in normal or low divalent cation concentrations. Much less, YO-PRO-1 was taken up by cells expressing human P2X$_7$ receptors, and human macrophages, than by cells expressing rP2X$_7$ receptors (FIG. 7A). On the other hand, there was significant uptake by hP2X$_7$-expressing cells and macrophages when these were compared with cells expressing P2X$_2$ receptors; this is clearly seen on the expanded scale of FIG. 7B. YO-PRO-1 uptake, measured 5 or 10 min after adding BzATP, was strongly dependent on the BzATP concentration (FIG. 7C). Cells expressing rP2X$_7$ receptors gave a larger 'maximal' response to BzATP, and showed YO-PRO-1 uptake at much lower concentrations of BzATP (FIG. 7C). It is unlikely that the lower YO-PRO 1 uptake into hP2X$_7$-expressing cells was due to a lower level of receptor expression than in rP2X$_7$-expressing cells, because the cation current induced by maximal concentrations of BZATP (30 $\mu$M for the rat, 300 $\mu$M for the rat) were not different (1869±286 pA vs 1777±342 pA, n=12). There is, on the other hand, quite good arrangement between the concentrations of BZATP required to induce cation current measured electrophysiologically (FIG. 6H) and YO-PRO uptake measured by fluorescence (FIG. 7C). These results are in general agreement with previous work which indicates that higher agonist concentrations are required to induce permeabilization of human macrophages than rodent macrophages (Blanchard et al, Blood 85:3173 (1995)).

Exchange of human and rat P2X$_7$ receptor C-terminal domains. The most obvious difference between the P2X$_7$ receptor and other P2X receptors is the induction by agonists of an increased permeability to very large ions, including propidium dyes (see Example 2). This difference is accounted for, at least in part, by the long C-terminal domain of the P2X$_7$ receptor because it largely disappears in a P2X$_7$ receptor in which this domain is greatly truncated (at residue 418). This suggested that the greater propidium uptake observed for the rP2X$_7$ receptor than the hP2X$_7$ might result from differences in this C-terminal domain. Therefore, the properties of cells expressing four different receptors: hP2X$_7$, rat P2X$_7$, h-rP2X$_7$ and r-hP2X$_7$, where the h-r and r-h forms were chimeras with exchanged C-terminal domains, were compared. These chimeras have completely exchanged cytoplasmic C-terminal domains (248 amino acids) because the point of exchange was within the second putative transmembrane domain (residue 347).

In electrophysiological experiments, all four proteins expressed similar peak currents. The deactivation kinetics were largely transferred by exchange of the C-terminal domain, in both directions. Thus, cells expressing h-rP2X$_7$ receptors showed currents in low divalent concentrations that did not decline for minutes after removal of the BzATP (FIG. 8A). The current measured at 30 s was 70±4 of peak, n=10). Conversely, r-hP2X$_7$ receptors gave currents that more closely resembled those of wildtype hP2X$_7$ receptors (FIG. 8A); the current measured at 30 s was 31±3 of peak, n=10). The difference in sensitivity to BZATP between human and rat receptors was also affected, but in this case the exchange was not reciprocal. Thus, the rat C-terminus on the human receptor (h-rP2X,) increased the sensitivity to BZATP, but the human C-terminus on the rat receptor (r-hP2X$_7$) did not reduce the sensitivity to BzATP (FIG. 8B). These experiments suggest that binding of BzATP and subsequent conformational changes leading to channel opening involve concerted conformational changes in both domains of the molecule.

Measurements of YO-PRO-1 uptake in cells expressing the chimeric receptors indicated that provision of the rat C-terminus domain to the human receptor (rP2X$_7$) significantly increased permeability to this large cation (FIG. 8C; measured 5 min after adding, a maximal concentration on BZATP). On the other hand, substituting the human C-terminus onto the rat receptor (r-hP2X$_7$) did not significantly reduce YO-PRO-1 uptake, as compared to that seen with wild-type rat receptor. The rat receptor truncated at residue 418 (P2X$_7$ΔC) showed very little YO-PRO uptake, even compared to the wildtype hP2X$_7$ receptor (FIG. 8C).

These experiments demonstrate three main functional differences between the rat and human P2X$_7$ receptors. The first is the lower sensitivity to agonists, notably BZATP, of the human receptor. This agonist sensitivity might have been expected to be determined by the presumed extracellular loop of the receptor, but such a simple interpretation is not consistent with the finding that the human receptor with the rat cytoplasmic C-terminus domain is as sensitive as the wildtype rat receptor (FIG. 8B). The second difference relates to the time for which the inward current flows following a brief application of agonist; the greatly prolonged currents observed in the rat P2X$_7$ receptor, and which distinguishes it dramatically from other P2X receptors (see Example 2), were much less obvious in the case of the human P2X$_7$ receptor (FIGS. 6A–C and 8A). The different rate at which the channel closes after removal of the agonist (deactivation) was largely transferred by exchange of the C-terminus domain, suggesting that this cytoplasmic part of the molecule is a determinant of channel closing. It has been shown previously that the prolonged component of the current in rP2X$_7$ receptors is associated with an increased conductance to large cations such as N-methyl-D-glucamine (see Example 2); if an initially small channel dilates into a larger pore, then this result implies that the C-terminal domain is a determinant of the rate of dilation.

The third large difference between species was the uptake of the propidium dye, YO-PRO-1. Complete transfer of this phenotype with the exchange of C-terminal domains was not observed, although one might have expected such a result if the slow deactivation kinetics and the larger YO-PRO-1 uptake are both related to formation of a large pore. However, the YO-PRO-1 uptake reflects the cell permeabilization during several minutes of the continued presence of BzATP, whereas the deactivation kinetics reflect the closure of ion conducting channels which have been opened by a very brief application of BzATP. The experiments have also shown that, in all the respects examined, the human P2X$_7$ receptor cloned from monocytes corresponds in its properties to the ATP receptor of the human macrophage. This is consistent with the macrophage receptor assembling as a homomultimer of P2X$_7$ subunits.

EXAMPLE 4

Immunohistochemistry

A rabbit polyclonal antiserum was raised against a synthetic peptide corresponding to the C-terminal 20 amino acids (KIRKEFPKTQGQYSGFKYPY) of the rat P2X$_7$ receptor. The antiserum was affinity purified on Sepharose 4B (Pharmacia) coupled with the synthetic peptide. Antisera was eluted with 3 M ammonium thiocyanate, 0.1 M Tris-HCl pH7.5, dialysed against phosphate buffered saline and concentrated to 1 mg/ml by microfiltration.

For immunohistochemistry, frozen sections were fixed for 10 min in ice cold acetone, washed in PBS and blocked with PBS containing 5% bovine serum albumin, 5% goat serum with 1% Triton X-100. After blocking, sections were incubated with anti-P2X$_7$ antibody at 10 mg/ml for 2 h at room temperature or 16 h at 4° C., then washed in PBS. The endogenous peroxidase activity was quenched by treating tissue sections with 1% hydrogen peroxide in PBS for 30 min. Staining was visualized by a 30 min incubation with biotinylated goat anti-rabbit antibody (Vector Laboratories, Burlingame, Calif.) followed by a 30 min incubation with horseradish peroxidase-streptavidin and development in diaminobenzidine, $H_2O_2$ and $NiCl_2$ (Vector Laboratories, Burlingame, Calif.) or 3-amino-9-ethyl-carbazole)(Zymed Laboratories Inc, South San Francisco, Calif.). Slides were counterstained with hematoxylin or cresyl violet before dehydrating and mounting with Entellan (Merck).

The specificity of the anti-P2X$_7$ antibody was tested by Western blotting. Cells were harvested with PBS containing 10 mM EDTA, washed twice and resuspended in PBS containing protease inhibitors (4 mM phenylmethylsulfonyl fluoride, 2 mg/ml pepstatin, 2 mg/ml leupeptin, 2 mg/ml trypsin inhibitor, 2 mg/ml aprotinin) (Sigma). Cells were freeze-thawed three times centrifuged 30 min at 4° C. and the membrane pellet was resuspended in lysis buffer (2% Triton X-100, 10 mM Tris-HCl, pH 8.5,150 mM NaCl, 1 mM $CaCl_2$) with protease inhibitors. After 1 h incubation on ice, the lysates were centrifugated at 40,000 rpm for 30 min, and the supernatants were analyzed by 10% SDS-polyacrylamide gel electrophoresis under reducing conditions. Separated proteins were transferred to a nitrocellulose membrane (Novex, San Diego, Calif.). The membrane was incubated with anti-P2X$_7$ antibody, followed by incubation with peroxidase-coupled sheep anti-rabbit IgG (Dako, Denmark) and developed using the ECL system (Amersham, Buckinghamshire, UK). Proteins extracted from HEK293 cells stably transfected with a rat P2X$_7$ receptor cDNA, or from CHO cells that were infected with the Semliki forest virus P2X$_7$ receptor construct showed a predominant 70 kDa band. The computed molecular weight of the P2X$_7$ receptor is 68,346 Da without glycosylation. No protein was identified in similar experiments using cells stably transfected with P2X$_2$ receptor cDNAs or from CHO cells infected by Semliki forest virus to express P2X$_2$ receptors. Immunoreactivity was not observed in sections stained with antibody that was preincubated 1 h with 10 mg/ml of the immunizing peptide.

Immunohistochemistry showed heavy expression in the ependyma of newborn and adult brain; the brain parenchyma showed no detectable expression except for the region around the area of necrosis which was present 24 h after occulsion of the middle cerebral artery. NTW8 cells, a mouse microglial cell line, strongly expressed the P2X$_7$ receptor mRNA and protein. Most bone marrow cells were positive by hybridization and also immunoreactive; this was observed also for marrow cells identified by their expression of other antigens as granulocytes, monocytes and B lymphocytes.

All documents cited above are hereby incorporated in their entirety by reference.

One skilled in the art will appreciate from a reading of this disclosure that various changes in form and detail can be made without departing from the true scope of the invention.

What is claimed is:

1. A method of screening a compound for its ability to modulate the permeabilizing activity of a mammalian P2X₇ receptor having the amino acid sequence of SEQ ID NO:17, 18 or 20 comprising:

contacting a cell, which is transformed with a construct comprising SEQ ID NO:17, 18 or 20 and expresses said P2X₇ receptor, with a P2X₇ receptor agonist, in the presence and absence of said compound, and assaying for an alteration in the permeabilizing activity of said P2X₇ receptor in the presence of said compound, and a reduction or increase in the permeabilizing activity of said P2X₇ receptor being indicative of a compound that modulates P2X₇ receptor permeabilizing activity.

2. The method of claim 1, wherein said agonist is ATP or BzATP.

3. A method of screening a compound for its ability to enhance the permeabilizing activity of a mammalian P2X₇ receptor having the amino acid sequence of SEQ ID NO:17, 18 or 20 comprising:

contacting a cell, which is transformed with a construct comprising SEQ ID NO:17, 18 or 20 and expresses said P2X₇ receptor, with said compound, assaying for permeabilizing activity of said P2X₇ receptor and comparing said permeabilizing activity with the permeabilizing activity of said P2X₇ receptor present in the absence of said compound, and wherein an increase in the permeabilizing activity of said P2X₇ receptor in the presence of said compound is indicative of a compound that enhances P2X₇ receptor permeabilizing activity.

4. A method of screening a compound for its ability to inhibit the permeabilizing activity of a mammalian P2X₇ receptor having the amino acid sequence of SEQ ID NO:17, 18 or 20 comprising:

contacting a cell, which is transformed with a construct comprising SEQ ID NO:17, 18 or 20 and expresses said P2X₇ receptor, with said compound and then with a P2X₇ receptor agonist, assaying for permeabilizing activity of said P2X₇ receptor and comparing said permeabilizing activity with the permeabilizing activity of said P2X₇ receptor present in the absence of said compound and presence of said agonist, and wherein a decrease in the permeabilizing activity of said P2X₇ receptor in the presence of said compound is indicative of a compound that inhibits P2X₇ receptor permeabilizing activity.

5. The method according to claim 4, wherein said agonist is ATP or BzATP.

6. The method according to claim 1, wherein said assaying is effected by monitoring the uptake into said cell of a detectable molecule.

7. The method according to claim 6, wherein said molecule is a fluorescent dye.

8. The method according to claim 7, wherein said dye is propidium iodide.

9. The method of claim 1, wherein said cell is an HEK293 cell.

10. The method of claim 1, wherein the P2X₇ receptor has the amino acid sequence of SEQ ID NO:18.

11. The method of claim 1, wherein the P2X₇ receptor has he amino acid sequence of SEQ ID NO:20.

12. The method of claim 4, wherein the P2X₇ receptor has the amino acid sequence of SEQ ID NO:18.

13. The method of claim 4 wherein the P2X₇ receptor has the amino acid sequence of SEQ ID NO:20.

* * * * *

UNITED STATES PATENT AND TRADEMARK OFFICE
CERTIFICATE OF CORRECTION

PATENT NO. : 6,509,163 B1
DATED : January 21, 2003
INVENTOR(S) : Buell et al.

It is certified that error appears in the above-identified patent and that said Letters Patent is hereby corrected as shown below:

Column 41,
Line 39, after "compound," delete "and".
Line 40, before "a reduction" insert -- wherein --.
Line 41, change "being" to -- is --.
Line 55, after "compound," delete "and".

Column 42,
Line 37, after "agonist," delete "and".

Signed and Sealed this

Eighth Day of July, 2003

JAMES E. ROGAN
*Director of the United States Patent and Trademark Office*

SEQUENCE LISTING

```
<160> NUMBER OF SEQ ID NOS: 20

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:Synthetic

<400> SEQUENCE: 1
ccacgcgtcg actagtacgg ggggggg                                        28

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:Synthetic

<400> SEQUENCE: 2
ggaattccac gcgtcgacta gtac                                           24

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 3
ggcgtatctg aagttgtagc                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 4
gtccagccgg cggaagctgt                                                20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence:Synthetic

<400> SEQUENCE: 5

Lys Ile Arg Lys Glu Phe Pro Lys Thr Gln Gly Gln Tyr Ser Gly Phe
  1               5                  10                  15

Lys Tyr Pro Tyr
            20

<210> SEQ ID NO 6
```

-continued

<211> LENGTH: 595
<212> TYPE: PRT
<213> ORGANISM: Artificial Sequence
<220> FEATURE:
<223> OTHER INFORMATION: Description of Artificial Sequence:Synthetic

<400> SEQUENCE: 6

```
Met Pro Ala Cys Cys Ser Trp Asn Asp Val Phe Gln Tyr Glu Thr Asn
 1               5                  10                  15

Lys Val Thr Arg Ile Gln Ser Val Asn Tyr Gly Thr Ile Lys Trp Ile
                20                  25                  30

Leu His Met Thr Val Phe Ser Tyr Val Ser Phe Ala Leu Met Ser Asp
            35                  40                  45

Lys Leu Tyr Gln Arg Lys Glu Pro Leu Ile Ser Val His Thr Lys
 50                  55                  60

Val Lys Gly Val Ala Glu Val Thr Glu Asn Val Thr Glu Gly Gly Val
 65                  70                  75                  80

Thr Lys Leu Val His Gly Ile Phe Asp Thr Ala Asp Tyr Thr Leu Pro
                85                  90                  95

Leu Gln Gly Asn Ser Phe Phe Val Met Thr Asn Tyr Leu Lys Ser Glu
            100                 105                 110

Gly Gln Glu Gln Lys Leu Cys Pro Glu Tyr Pro Ser Arg Gly Lys Gln
        115                 120                 125

Cys His Ser Asp Gln Gly Cys Ile Lys Gly Trp Met Asp Pro Gln Ser
130                 135                 140

Lys Gly Ile Gln Thr Gly Arg Cys Ile Pro Tyr Asp Gln Lys Arg Lys
145                 150                 155                 160

Thr Cys Glu Ile Phe Ala Trp Cys Pro Ala Glu Glu Gly Lys Glu Ala
                165                 170                 175

Pro Arg Pro Ala Leu Leu Arg Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Met Asn Ile Ser Cys Thr Phe His Lys Thr Trp Asn Pro
210                 215                 220

Gln Cys Pro Ile Phe Arg Leu Gly Asp Ile Phe Gln Glu Ile Gly Glu
225                 230                 235                 240

Asn Phe Thr Glu Val Ala Val Gln Gly Gly Ile Met Gly Ile Glu Ile
                245                 250                 255

Tyr Trp Asp Cys Asn Leu Asp Ser Trp Ser His Arg Cys Gln Pro Lys
            260                 265                 270

Tyr Ser Phe Arg Arg Leu Asp Asp Lys Tyr Thr Asn Glu Ser Leu Phe
        275                 280                 285

Pro Gly Tyr Asn Phe Arg Tyr Ala Lys Tyr Tyr Lys Glu Asn Gly Met
290                 295                 300

Glu Lys Arg Thr Leu Ile Lys Ala Phe Gly Val Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Thr Val Cys Ile Asp
            340                 345                 350

Leu Ile Ile Asn Thr Tyr Ala Ser Thr Cys Cys Arg Ser Arg Val Tyr
        355                 360                 365

Pro Ser Cys Lys Cys Cys Glu Pro Cys Ala Val Asn Glu Tyr Tyr Tyr
370                 375                 380
```

-continued

```
Arg Lys Lys Cys Glu Pro Ile Val Glu Pro Lys Pro Thr Leu Lys Tyr
385                 390                 395                 400

Val Ser Phe Val Asp Glu Pro His Ile Trp Met Val Asp Gln Gln Leu
            405                 410                 415

Leu Gly Lys Ser Leu Gln Asp Val Lys Gly Gln Glu Val Pro Arg Pro
            420                 425                 430

Gln Thr Asp Phe Leu Glu Leu Ser Arg Leu Ser Leu Ser Leu His His
            435                 440                 445

Ser Pro Pro Ile Pro Gly Gln Pro Glu Met Gln Leu Leu Gln Ile
    450                 455                 460

Glu Ala Val Pro Arg Ser Arg Asp Ser Pro Asp Trp Cys Gln Cys Gly
465                 470                 475                 480

Asn Cys Leu Pro Ser Gln Leu Pro Glu Asn Arg Arg Ala Leu Glu Glu
            485                 490                 495

Leu Cys Cys Arg Arg Lys Pro Gly Gln Cys Ile Thr Thr Ser Glu Leu
            500                 505                 510

Phe Ser Lys Ile Val Leu Ser Arg Glu Ala Leu Gln Leu Leu Leu Leu
            515                 520                 525

Tyr Gln Glu Pro Leu Leu Ala Leu Glu Gly Glu Ala Ile Asn Ser Lys
            530                 535                 540

Leu Arg His Cys Ala Tyr Arg Ser Tyr Ala Thr Trp Arg Phe Val Ser
545                 550                 555                 560

Gln Asp Met Ala Asp Phe Ala Ile Leu Pro Ser Cys Cys Arg Trp Lys
                565                 570                 575

Ile Arg Lys Glu Phe Pro Lys Thr Gln Gly Gln Tyr Ser Gly Phe Lys
            580                 585                 590

Tyr Pro Tyr
        595

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:Synthetic

<400> SEQUENCE: 7

Thr Lys Val Lys Gly
  1               5

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:Synthetic

<400> SEQUENCE: 8

Cys His Ser Asp
  1

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 9
```

```
Ala Trp Cys Pro Glu Gly
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:Synthetic

<400> SEQUENCE: 10

Leu Ile Lys Asn
  1

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:Synthetic

<400> SEQUENCE: 11

Cys Pro Ile Phe Arg Leu Gly
  1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:Synthetic

<400> SEQUENCE: 12

Pro Lys Tyr Ser Phe Arg Arg Leu Asp
  1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:Synthetic

<400> SEQUENCE: 13

Ala Lys Tyr Tyr Lys
  1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 14

Arg Thr Leu Ile Lys Ala
  1               5

<210> SEQ ID NO 15
<211> LENGTH: 472
<212> TYPE: PRT
<213> ORGANISM: Artificial Sequence
<220> FEATURE:
<223> OTHER INFORMATION: Description of Artificial Sequence:Synthetic

<400> SEQUENCE: 15

Met Val Arg Arg Leu Ala Arg Gly Cys Trp Ser Ala Phe Trp Asp Tyr
```

-continued

```
  1               5                    10                   15
Glu Thr Pro Lys Val Ile Val Arg Asn Arg Leu Gly Phe Val
            20                  25                  30

His Arg Met Val Gln Leu Leu Ile Leu Leu Tyr Phe Val Trp Tyr Val
            35                  40                  45

Phe Ile Val Gln Lys Ser Tyr Gln Asp Ser Glu Thr Gly Pro Glu Ser
 50                  55                  60

Ser Ile Ile Thr Lys Val Lys Gly Ile Thr Met Ser Glu Asp Lys Val
 65                  70                  75                  80

Trp Asp Val Glu Glu Tyr Val Lys Pro Glu Gly Ser Val Val
                85                  90                  95

Ser Ile Ile Thr Arg Ile Glu Val Thr Pro Ser Gln Thr Leu Gly Thr
            100                 105                 110

Cys Pro Glu Ser Met Arg Val His Ser Ser Thr Cys His Ser Asp Asp
            115                 120                 125

Asp Cys Ile Ala Gly Gln Leu Asp Met Gln Gly Asn Gly Ile Arg Thr
 130                 135                 140

Gly His Cys Val Pro Tyr Tyr His Gly Asp Ser Lys Thr Cys Glu Val
145                 150                 155                 160

Ser Ala Trp Cys Pro Val Glu Asp Gly Thr Ser Asp Asn His Phe Leu
            165                 170                 175

Gly Lys Met Ala Pro Asn Phe Thr Ile Leu Ile Lys Asn Ser Ile His
            180                 185                 190

Tyr Pro Lys Phe Lys Phe Ser Lys Gly Asn Ile Ala Ser Gln Lys Ser
            195                 200                 205

Asp Tyr Leu Lys His Cys Thr Phe Asp Gln Asp Ser Asp Pro Tyr Cys
            210                 215                 220

Pro Ile Phe Arg Leu Gly Phe Ile Val Glu Lys Ala Gly Glu Asn Phe
225                 230                 235                 240

Thr Glu Leu Ala His Lys Gly Gly Val Ile Gly Val Ile Ile Asn Trp
            245                 250                 255

Asn Cys Asp Leu Asp Leu Ser Glu Glu Cys Asn Pro Lys Tyr Ser
            260                 265                 270

Phe Arg Arg Leu Asp Pro Lys Tyr Asp Pro Ala Ser Ser Gly Tyr Asn
            275                 280                 285

Phe Arg Phe Ala Lys Tyr Tyr Lys Ile Asn Gly Thr Thr Thr Arg
290                 295                 300

Thr Leu Ile Lys Ala Tyr Gly Ile Arg Ile Asp Val Ile Val His Gly
305                 310                 315                 320

Gln Ala Gly Lys Phe Ser Leu Ile Pro Thr Ile Ile Asn Leu Ala Thr
            325                 330                 335

Ala Leu Thr Ser Ile Gly Val Gly Ser Phe Leu Cys Asp Trp Ile Leu
            340                 345                 350

Leu Thr Phe Met Asn Lys Asn Lys Leu Tyr Ser His Lys Lys Phe Asp
            355                 360                 365

Lys Val Arg Thr Pro Lys His Pro Ser Ser Arg Trp Pro Val Thr Leu
            370                 375                 380

Ala Leu Val Leu Gly Gln Ile Pro Pro Pro Ser His Tyr Ser Gln
385                 390                 395                 400

Asp Gln Pro Pro Ser Pro Ser Gly Glu Gly Pro Thr Leu Gly Glu
            405                 410                 415

Gly Ala Glu Leu Pro Leu Ala Val Gln Ser Pro Arg Pro Cys Ser Ile
            420                 425                 430
```

Ser Ala Leu Thr Glu Gln Val Val Asp Thr Leu Gly Gln His Met Gly
        435                 440                 445

Gln Arg Pro Pro Val Pro Glu Pro Ser Gln Gln Asp Ser Thr Ser Thr
    450                 455                 460

Asp Pro Lys Gly Leu Ala Gln Leu
465                 470

<210> SEQ ID NO 16
<211> LENGTH: 3540
<212> TYPE: DNA
<213> ORGANISM: Artificial Sequence
<220> FEATURE:
<223> OTHER INFORMATION: Description of Artificial Sequence:Synthetic

<400> SEQUENCE: 16

| | | | | | |
|---|---|---|---|---|---|
| ttaaacgttc | ctgctaagta | atcggtgtgc | tttcttcggc | tactcttcgg | tgggggcttg | 60 |
| ctgtggtcta | gcctgggaag | gtctagccca | ggtcccgccg | aaacagagtg | agcctgtcgc | 120 |
| catgccggct | tgctgcagct | ggaacgatgt | ctttcagtat | gagacaaaca | aagtcacccg | 180 |
| gatccagagc | gtgaattacg | gcaccatcaa | gtggatcttg | cacatgaccg | tcttttccta | 240 |
| cgttagcttt | gctttgatga | gcgacaagct | atatcagcgg | aaggagcccc | ttatcagctc | 300 |
| tgtgcacacc | aaggtcaaag | gcgttgcaga | ggtgacagag | aatgtcacgg | agggcggggt | 360 |
| gacgaagtta | gtacacggca | tcttcgacac | ggccgactac | accctccctt | gcaggggaa | 420 |
| ctcgttcttt | gtaatgacaa | attatctcaa | gtcagaaggc | caagaacaga | agctgtgtcc | 480 |
| tgagtatccc | agccgcggta | aacagtgcca | ttctgaccag | ggttgtataa | aaggatggat | 540 |
| ggacccacaa | agtaaaggaa | tccagaccgg | caggtgtata | ccttacgacc | agaagaggaa | 600 |
| gacctgtgaa | atctttgcct | ggtgtcctgc | tgaggaaggg | aaagaagccc | cacggcctgc | 660 |
| actcttgagg | agcgccgaaa | acttcaccgt | actcatcaag | aacaatatcg | acttcccggg | 720 |
| ccacaactat | actacgagaa | acatcttacc | aggtatgaac | atctcttgta | cctttcacaa | 780 |
| gacttggaac | cctcagtgtc | ccatcttccg | gctaggggac | atcttccagg | aaatcggaga | 840 |
| gaactttaca | gaggtggcag | ttcagggagg | aatcatgggc | attgagatct | actgggactg | 900 |
| caacctggac | agctggtccc | atcgctgtca | acccaaatac | agcttccgcc | ggctggacga | 960 |
| caagtacacc | aatgagtccc | tgttccctgg | ctacaacttc | agatacgcca | agtactataa | 1020 |
| ggaaaatggc | atggaaaagc | ggacattgat | caaagccttc | ggcgtgcgtt | ttgacatcct | 1080 |
| ggttttttggc | actggaggaa | agtttgacat | catccagttg | gttgtgtaca | ttggatccac | 1140 |
| cctgtcctat | ttcggtttgg | ccaccgtgtg | tattgacttc | atcatcaaca | cgtatgccag | 1200 |
| tacctgctgc | aggtcacgtg | tttacccctc | ctgtaagtgc | tgcgagccct | gtgcagtgaa | 1260 |
| tgagtactac | tacagaaaga | agtgtgagcc | catcgtggag | cccaagccga | cgttaaagta | 1320 |
| tgtgtccttt | gtggacgagc | cccacatttg | gatggtggac | cagcagctgc | ttgggaaaag | 1380 |
| tctgcaagat | gtcaaaggtc | aagaggtccc | gagaccccag | acggacttct | ggaactgtc | 1440 |
| taggctctcc | ctctctctcc | accactcacc | cccaattcct | ggacaacctg | aggaaatgca | 1500 |
| gctgctccag | atagaagcgg | ttcctaggtc | caggacagc | ccagattggt | gccagtgtgg | 1560 |
| aaactgcctc | ccgtctcaac | taccagagaa | ccgcagggcc | ctggaggagc | tgtgctgccg | 1620 |
| gaggaagcca | ggacagtgca | tcactacctc | tgagctcttc | agtaagatcg | tgctatccag | 1680 |
| agaggccctg | cagtcctcc | tgctctacca | ggagcccttg | ctggcgctgg | agggagaggc | 1740 |
| catcaacagc | aagctgcgac | actgtgcgta | caggagctat | gccacctggc | gctttgtctc | 1800 |

```
ccaagacatg gccgactttg ccattctgcc cagctgctgc cgctggaaga tccggaagga    1860
gttccccaag acccaggggc agtacagtgg cttcaagtat ccctactgac agtatggctg    1920
ccacattatg gtgactcata atatagcatt ctcttggaaa gacttagaga cacactttca    1980
gccaaagggg aacttaagtc ttcctccctc gtaagccgtg ttgaagggat tgttaggcca    2040
atggcaagca catgaacccc tctccacgtg gatgagaaac agatgcagat ctgagcctgc    2100
ggcttgacct ggactgcggt gccacccaca gcctataacg tatacacagg ctcctcgaat    2160
cccgaccttc cccaactcac ttcctctgaa ctagcattgt ggagacggtg aaggtgtttt    2220
ctctcccgtc catgtcttcc cagcttcctg gatacagagg cccattcctg aaaaccaaac    2280
cttttgagat tcgagagtac tctgagaaat gaaatatggc cacaaattct ttgacgtcct    2340 ccacccccaac ccaaccccctc aagacccaaa ggtgtcgttt ccctccccca ttacgggcaa    2400
ctctggcggc ttcatccagt agcggatgtg acgtcacatg tattgtttca ggccctagtt    2460
ttaagaggct aacaacttcc aattcctgtt gaacgcttgc tgagaggaag ccaggcaagt    2520
taagagcaca actatagggg cttctcggct gtgaggaagc ccgagaagct ccaggggaa    2580 gtaatcaacc tgagccagct catcaccaga agctgccacc ggcaggtgat tccagacacg    2640
acacgtgact gaaactgcag gagacgaact gcgcatgtca acccagagga ccactctgct    2700
gccttgtcgt tacatgtggg gagtgcggtc accacacagc aacaggcaac cggagcaagg    2760
gatgctaacc gaggcccgag tcactgcaaa gcgtagagac tccttatatc gggcaacttt    2820
aagaggtcac attaaccaga ctagaagcca tcgcatctaa ccgcatacca gacacagtct    2880
gacgcctcat tgctatgcta tggttctaag tgactgctat tggcagaaac cactaaaagc    2940
cgcctctgtg cctttaacgt cctggactga acagccaatg agtccgaggc aatctaatgc    3000
ctcagcctag tgcctttggg gggcgggggg tcagaagagg gtgtctcctg gaactggaat    3060
tgcaggtgga tatgaggtac cgtgtgggtc ctgggaagtg aacttgagcc ctctggagca    3120
gcagccggtg ctcttaacca ctgagccgtc cctacacctt cacaaccaca tcttaaaaat    3180
cataatcata atagagaaaa agagagggga agagcgcctg gggaggtggt tcagtgggta    3240
agagcacaag catgaggacc tttgttggga tcacagcatc cacctaaagt ttggatgtgg    3300
cttggtagag acaggagggt gggggtgggg gggtgagct tgccatgtaa tctgatgacc    3360
ttgaacccca tggtgaatgt ggagaatcac gttctctgac ttccacatgg acctcacaca    3420
cacaccacac accacacaga cacagacaca ctaccaccac aaccacaagc acacatacac    3480
atgaagacac acagagacat atacacacta ccactaccac cacaaccaca cactcacaca    3540
```

<210> SEQ ID NO 17
<211> LENGTH: 595
<212> TYPE: PRT
<213> ORGANISM: Artificial Sequence
<220> FEATURE:
<223> OTHER INFORMATION: Description of Artificial Sequence:Synthetic

<400> SEQUENCE: 17

```
Met Pro Ala Cys Cys Ser Trp Asn Asp Val Phe Gln Tyr Glu Thr Asn
 1               5                  10                  15

Lys Val Thr Arg Ile Gln Ser Val Asn Tyr Gly Thr Ile Lys Trp Ile
            20                  25                  30

Leu His Met Thr Val Phe Ser Tyr Val Ser Phe Ala Leu Met Ser Asp
        35                  40                  45

Lys Leu Tyr Gln Arg Lys Glu Pro Leu Ile Ser Ser Val His Thr Lys
```

-continued

```
                50                  55                  60
Val Lys Gly Val Ala Glu Val Thr Glu Asn Val Thr Glu Gly Gly Val
 65                  70                  75                  80

Thr Lys Leu Val His Gly Ile Phe Asp Thr Ala Asp Tyr Thr Leu Pro
                 85                  90                  95

Leu Gln Gly Asn Ser Phe Phe Val Met Thr Asn Tyr Leu Lys Ser Glu
                100                 105                 110

Gly Gln Glu Gln Lys Leu Cys Pro Glu Tyr Pro Ser Arg Gly Lys Gln
                115                 120                 125

Cys His Ser Asp Gln Gly Cys Ile Lys Gly Trp Met Asp Pro Gln Ser
                130                 135                 140

Lys Gly Ile Gln Thr Gly Arg Cys Ile Pro Tyr Asp Gln Lys Arg Lys
145                 150                 155                 160

Thr Cys Glu Ile Phe Ala Trp Cys Pro Ala Glu Gly Lys Glu Ala
                165                 170                 175

Pro Arg Pro Ala Leu Leu Arg Ser Ala Glu Asn Phe Thr Val Leu Ile
                180                 185                 190

Lys Asn Asn Ile Asp Phe Pro Gly His Asn Tyr Thr Thr Arg Asn Ile
                195                 200                 205

Leu Pro Gly Met Asn Ile Ser Cys Thr Phe His Lys Thr Trp Asn Pro
                210                 215                 220

Gln Cys Pro Ile Phe Arg Leu Gly Asp Ile Phe Gln Glu Ile Gly Glu
225                 230                 235                 240

Asn Phe Thr Glu Val Ala Val Gln Gly Gly Ile Met Gly Ile Glu Ile
                245                 250                 255

Tyr Trp Asp Cys Asn Leu Asp Ser Trp Ser His Arg Cys Gln Pro Lys
                260                 265                 270

Tyr Ser Phe Arg Arg Leu Asp Asp Lys Tyr Thr Asn Glu Ser Leu Phe
                275                 280                 285

Pro Gly Tyr Asn Phe Arg Tyr Ala Lys Tyr Tyr Lys Glu Asn Gly Met
                290                 295                 300

Glu Lys Arg Thr Leu Ile Lys Ala Phe Gly Val Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Thr Val Cys Ile Asp
                340                 345                 350

Leu Ile Ile Asn Thr Tyr Ala Ser Thr Cys Cys Arg Ser Arg Val Tyr
                355                 360                 365

Pro Ser Cys Lys Cys Cys Glu Pro Cys Ala Val Asn Glu Tyr Tyr Tyr
                370                 375                 380

Arg Lys Lys Cys Glu Pro Ile Val Glu Pro Lys Pro Thr Leu Lys Tyr
385                 390                 395                 400

Val Ser Phe Val Asp Glu Pro His Ile Trp Met Val Asp Gln Gln Leu
                405                 410                 415

Leu Gly Lys Ser Leu Gln Asp Val Lys Gly Gln Glu Val Pro Arg Pro
                420                 425                 430

Gln Thr Asp Phe Leu Glu Leu Ser Arg Leu Ser Leu Ser Leu His His
                435                 440                 445

Ser Pro Pro Ile Pro Gly Gln Pro Glu Glu Met Gln Leu Leu Gln Ile
                450                 455                 460

Glu Ala Val Pro Arg Ser Arg Asp Ser Pro Asp Trp Cys Gln Cys Gly
465                 470                 475                 480
```

```
Asn Cys Leu Pro Ser Gln Leu Pro Glu Asn Arg Arg Ala Leu Glu Glu
                485                 490                 495

Leu Cys Cys Arg Arg Lys Pro Gly Gln Cys Ile Thr Thr Ser Glu Leu
            500                 505                 510

Phe Ser Lys Ile Val Leu Ser Arg Glu Ala Leu Gln Leu Leu Leu Leu
        515                 520                 525

Tyr Gln Glu Pro Leu Leu Ala Leu Glu Gly Glu Ala Ile Asn Ser Lys
    530                 535                 540

Leu Arg His Cys Ala Tyr Arg Ser Tyr Ala Thr Trp Arg Phe Val Ser
545                 550                 555                 560

Gln Asp Met Ala Asp Phe Ala Ile Leu Pro Ser Cys Cys Arg Trp Lys
                565                 570                 575

Ile Arg Lys Glu Phe Pro Lys Thr Gln Gly Gln Tyr Ser Gly Phe Lys
            580                 585                 590

Tyr Pro Tyr
        595

<210> SEQ ID NO 18
<211> LENGTH: 595
<212> TYPE: PRT
<213> ORGANISM: Artificial Sequence
<220> FEATURE:
<223> OTHER INFORMATION: Description of Artificial Sequence:Synthetic

<400> SEQUENCE: 18

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240
```

```
Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys His Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
                340                 345                 350

Phe Leu Ile Asp Thr Tyr Ser Ser Asn Cys Cys Arg Ser His Ile Tyr
            355                 360                 365

Pro Trp Cys Lys Cys Gln Pro Cys Val Val Asn Glu Tyr Tyr Tyr
        370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Leu
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 19
<211> LENGTH: 1853
<212> TYPE: DNA
<213> ORGANISM: Artificial Sequence
<220> FEATURE:
<223> OTHER INFORMATION: Description of Artificial Sequence:Synthetic

<400> SEQUENCE: 19
```

```
aaaacgcagg gagggaggct gtcaccatgc cggcctgctg cagctgcagt gatgttttcc      60
agtatgagac gaacaaagtc actcggatcc agagcatgaa ttatggcacc attaagtggt     120
tcttccacgt gatcatcttt tcctacgttt gctttgctct ggtgagtgac aagctgtacc     180
agcggaaaga gcctgtcatc agttctgtgc acaccaaggt gaaggggata gcagaggtga     240
aagaggagat cgtggagaat ggagtgaaga agttggtgca cagtgtcttt gacaccgcag     300
actacacctt ccctttgcag gggaactctt tcttcgtgat gacaaacttt ctcaaaacag     360
aaggccaaga gcagcggttg tgtcccgagt atcccacccg caggacgctc tgttcctctg     420
accgaggttg taaaaaggga tggatggacc cgcagagcaa aggaattcag accggaaggt     480
gtgtagtgca tgaagggaac cagaagacct gtgaagtctc tgcctggtgc ccatcgagg      540
cagtggaaga ggccccccgg cctgctctct tgaacagtgc cgaaaacttc actgtgctca     600
tcaagaacaa tatcgacttc cccggccaca actacaccac gagaaacatc ctgccaggtt     660
taaacatcac ttgtaccttc acaagactca gaatccaca gtgtcccatt ttccgactag      720
gagacatctt ccgagaaaca ggcgataatt tttcagatgt ggcaattcag ggcggaataa     780
tgggcattga gatctactgg gactgcaacc tagaccgttg gttccatcac tgccatccca     840
aatacagttt ccgtcgcctt gacgacaaga ccaccaacgt gtccttgtac cctggctaca     900
acttcagata cgccaagtac tacaaggaaa acaatgttga gaaacggact ctgataaaag     960
tcttcgggat ccgttttgac atcctggttt ttggcaccgg aggaaaattt gacattatcc    1020
agctggttgt gtacatcggc tcaaccctct cctacttcgg tctggccgct gtgttcatcg    1080
acttcctcat cgacacttac tccagtaact gctgtcgctc ccatatttat ccctggtgca    1140
agtgctgtca gccctgtgtg gtcaacgaat actactacag gaagaagtgc gagtccattg    1200
tggagccaaa gccgacatta agtatgtgt cctttgtgga tgaatcccac attaggatgg     1260
tgaaccagca gctactaggg agaagtctgc aagatgtcaa gggccaagaa gtcccaagac    1320
ctgcgatgga cttcacagat ttgtccaggc tgccccctgc cctccatgac acaccccga     1380
ttcctggaca accagaggag atacagctgc ttagaaagga ggcgactcct agatccaggg    1440
atagcccgt ctggtgccag tgtggaagct gcctcccatc tcaactccct gagagccaca     1500
ggtgcctgga ggagctgtgc tgccggaaaa agccggggc ctgcatcacc acctcagagc     1560
tgttcaggaa gctggtcctg tccagacacg tcctgcagtt cctcctgctc taccaggagc    1620
ccttgctggc gctggatgtg gattccacca acagccggct gcggcactgt gcctacaggt    1680
gctacgccac ctggcgcttc ggctcccagg acatggctga cttttgccatc ctgcccagct    1740
gctgccgctg gaggatccgg aaagagtttc gaagagtgt agggcagtac agtggcttca    1800
agagtcctta ctgaagccag gcaccgtggc tcacgtctgt aatcccacct ttt            1853
```

<210> SEQ ID NO 20
<211> LENGTH: 595
<212> TYPE: PRT
<213> ORGANISM: Artificial Sequence
<220> FEATURE:
<223> OTHER INFORMATION: Description of Artificial Sequence:Synthetic

<400> SEQUENCE: 20

Met Pro Ala Cys Cys Ser Cys Ser Asp Val Phe Gln Tyr Glu Thr Asn
 1               5                  10                  15

Lys Val Thr Arg Ile Gln Ser Met Asn Tyr Gly Thr Ile Lys Trp Phe
             20                  25                  30

-continued

```
Phe His Val Ile Ile Phe Ser Tyr Val Cys Phe Ala Leu Val Ser Asp
         35                  40                  45

Lys Leu Tyr Gln Arg Lys Glu Pro Val Ile Ser Ser Val His Thr Lys
     50                  55                  60

Val Lys Gly Ile Ala Glu Val Lys Glu Glu Ile Val Glu Asn Gly Val
 65                  70                  75                  80

Lys Lys Leu Val His Ser Val Phe Asp Thr Ala Asp Tyr Thr Phe Pro
                 85                  90                  95

Leu Gln Gly Asn Ser Phe Phe Val Met Thr Asn Phe Leu Lys Thr Glu
             100                 105                 110

Gly Gln Glu Gln Arg Leu Cys Pro Glu Tyr Pro Thr Arg Arg Thr Leu
             115                 120                 125

Cys Ser Ser Asp Arg Gly Cys Lys Lys Gly Trp Met Asp Pro Gln Ser
     130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                 165                 170                 175

Pro Arg Pro Ala Leu Leu Asn Ser Ala Glu Asn Phe Thr Val Leu Ile
             180                 185                 190

Lys Asn Asn Ile Asp Phe Pro Gly His Asn Tyr Thr Thr Arg Asn Ile
     195                 200                 205

Leu Pro Gly Leu Asn Ile Thr Cys Thr Phe His Lys Thr Gln Asn Pro
210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                 245                 250                 255

Tyr Trp Asp Cys Asn Leu Asp Arg Trp Phe His His Cys His Pro Lys
             260                 265                 270

Tyr Ser Phe Arg Arg Leu Asp Asp Lys Thr Thr Asn Val Ser Leu Tyr
     275                 280                 285

Pro Gly Tyr Asn Phe Arg Tyr Ala Lys Tyr Tyr Lys Glu Asn Asn Val
290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                 325                 330                 335

Ile Gly Ser Thr Leu Ser Tyr Phe Gly Leu Ala Ala Val Phe Ile Asp
             340                 345                 350

Phe Leu Ile Asp Thr Tyr Ser Ser Asn Cys Cys Arg Ser His Ile Tyr
     355                 360                 365

Pro Trp Cys Lys Cys Cys Gln Pro Cys Val Val Asn Glu Tyr Tyr Tyr
370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                 405                 410                 415

Leu Gly Arg Ser Leu Gln Asp Val Lys Gly Gln Glu Val Pro Arg Pro
             420                 425                 430

Ala Met Asp Phe Thr Asp Leu Ser Arg Leu Pro Leu Ala Leu His Asp
     435                 440                 445

Thr Pro Pro Ile Pro Gly Gln Pro Glu Glu Ile Gln Leu Leu Arg Lys
```

-continued

```
                    450                 455                 460
Glu Ala Thr Pro Arg Ser Arg Asp Ser Pro Val Trp Cys Gln Cys Gly
465                 470                 475                 480
Ser Cys Leu Pro Ser Gln Leu Pro Glu Ser His Arg Cys Leu Glu Glu
                485                 490                 495
Leu Cys Cys Arg Lys Lys Pro Gly Ala Cys Ile Thr Thr Ser Glu Leu
            500                 505                 510
Phe Arg Lys Leu Val Leu Ser Arg His Val Leu Gln Phe Leu Leu Leu
        515                 520                 525
Tyr Gln Glu Pro Leu Leu Ala Leu Asp Val Asp Ser Thr Asn Ser Arg
    530                 535                 540
Leu Arg His Cys Ala Tyr Arg Cys Tyr Ala Thr Trp Arg Phe Gly Ser
545                 550                 555                 560
Gln Asp Met Ala Asp Phe Ala Ile Leu Pro Ser Cys Cys Arg Trp Arg
                565                 570                 575
Ile Arg Lys Glu Phe Pro Lys Ser Val Gly Gln Tyr Ser Gly Phe Lys
                580                 585                 590
Ser Pro Tyr
        595
```